US012734221B2

(12) United States Patent
Prasad et al.

(10) Patent No.: US 12,734,221 B2
(45) Date of Patent: Sep. 15, 2026

(54) CORE FOUR DIETARY SUPPLEMENT SYSTEM

(71) Applicants: Kedar Prasad, San Rafael, CA (US); Tyler M Delarosa, New York, NY (US)

(72) Inventors: Kedar Prasad, San Rafael, CA (US); Tyler M Delarosa, New York, NY (US)

( * ) Notice: Subject to any disclaimer, the term of this patent is extended or adjusted under 35 U.S.C. 154(b) by 0 days.

(21) Appl. No.: 18/831,878

(22) Filed: Oct. 20, 2025

(65) Prior Publication Data

US 2026/0077022 A1 Mar. 19, 2026

Related U.S. Application Data

(63) Continuation-in-part of application No. 18/831,490, filed on Feb. 25, 2025, and a continuation-in-part of application No. 18/445,785, filed on Feb. 1, 2024, now Pat. No. 12,447,174, and a continuation-in-part of application No. 18/445,710, filed on Dec. 20, 2023, now abandoned, and a continuation-in-part of application No. 17/835,689, filed on Jun. 8, 2022, now Pat. No. 11,819,538.

(51) Int. Cl.

| | |
|---|---|
| ***A61K 38/39*** | (2006.01) |
| ***A61K 31/202*** | (2006.01) |
| ***A61K 35/00*** | (2006.01) |
| ***A61K 35/742*** | (2015.01) |
| ***A61K 35/745*** | (2015.01) |
| ***A61K 35/747*** | (2015.01) |
| ***A61K 36/064*** | (2006.01) |
| ***A61K 45/06*** | (2006.01) |

(52) U.S. Cl.

CPC ............ *A61K 38/39* (2013.01); *A61K 31/202* (2013.01); *A61K 35/742* (2013.01); *A61K 35/745* (2013.01); *A61K 35/747* (2013.01); *A61K 36/064* (2013.01); *A61K 45/06* (2013.01); *A61K 2035/115* (2013.01)

(58) Field of Classification Search

None

See application file for complete search history.

(56) References Cited

PUBLICATIONS

Screen captures from Vimeo video clip entitled "Engage Core4 Presentation With Dr Prasad", X pages, uploaded on Apr. 14, 2024 by user "Jessica Maldonado" (retrieved from Internet on Feb. 5, 2026: https://vimeo.com/934523079 (Year: 2014).*

Collagen Daily. Product Information Page [online]. Engage Global, 2026 [retrieved on Feb. 5, 2026]. Retrieved from the Internet: https://microdaily.com/ladyw/product/active-products/engage-global-collagen-daily-skuusen34815-id415 (Year: 2026).*

Micro Daily Hydro EMF. Product Information Page [online]. Engage Global, 2026 [retrieved on Feb. 5, 2026]. Retrieved from the Internet: https://microdaily.com/ladyw/product/active-products/engage-global-micro-daily-hydro-emf-skuusen35100-id452 (Year: 2026).*

Probiotic Daily. Product Information Page [online]. Engage Global, 2026 [retrieved on Feb. 5, 2026]. Retrieved from the Internet: https://microdaily.com/ladyw/product/active-products/engage-global-probiotic-daily-skuusen34905-id422 (Year: 2026).*

Omega3 Daily. Product Information Page [online]. Engage Global, 2026 [retrieved on Feb. 5, 2026]. Retrieved from the Internet: https://microdaily.com/ladyw/product/active-products/engage-global-omega-3-daily-skuusen53200-id455 (Year: 2026).*

* cited by examiner

*Primary Examiner* — Sudhakar Katakam
*Assistant Examiner* — Zachary J Miknis
(74) *Attorney, Agent, or Firm* — Dan Delarosa, Esq

(57) ABSTRACT

A core four dietary supplement system comprising at least one collagen system, at least one microdaily EMF system, at least one omega-3 system and at least one prebiotic and probiotic system with acid and heat resistant bacteria, is provided.

14 Claims, No Drawings

CORE FOUR DIETARY SUPPLEMENT SYSTEM

RELATED APPLICATIONS

This application is a continuation-in-part of U.S. application Ser. No. 17/835,689 entitled "COLLAGEN DAILY WITH ENZYME INHIBITORS FOR ANTI-AGING" filed Jun. 8, 2022, a continuation-in-part of U.S. application Ser. No. 18/445,785 entitled "MICRODAILY EMF" filed Feb. 1, 2024 which has now been granted a Notice of Allowance, a continuation-in-part of U.S. application Ser. No. 18/445,710 entitled "COMPOSITION CONTAINING OMEGA-3 FOR BRAIN AND HEART HEALTH, AND GLUCOSE METABOLISM" filed Dec. 20, 2023 and a continuation-in-part of U.S. application Ser. No. 18/831,490 entitled "PREBIOTIC AND PROBIOTIC FORMULATION CONTAINING ACID AND HEAT RESISTANT BACTERIA" filed on Feb. 25, 2025. This application incorporates all four of these applications by reference.

BACKGROUND OF THE INVENTION

Collagen:

After 30 years of age, a gradual decline in the levels of collagen, elastin, and hyaluronic acid occurs. This decline in the levels of collagen, elastin, and hyaluronic acid is due to their enhanced degradation by the enzymes collagenase, matrix metallopeptidases (MMPs), elastase, and hyaluronidase. Decreased levels of collagen causes thinning of the skin, reduced levels of elastin causes loss of elasticity of the skin, and reduction in the levels of hyaluronic acid causes dehydration of the skin. Because of the above changes, the skin becomes thinner, looks sagging, drier, and wrinkled. In addition to skin aging, bones become weaker and fragile, cartilage in the joints becomes degenerated, decrease in muscle function reduces mobility and balance. These studies suggest that maintaining sufficient levels of collagen, elastin, and hyaluronic acid may reduce the rate of aging of the skin, age-related dysfunction of other organs, and improve your health and appearance. However, there are no effective and prolonged ways to improve the levels of collagen, elastin, and hyaluronic acid in humans.

Use of commercial collagen peptides has improved the levels of collagen, elastin, and hydration somewhat, but these effects on the skin are reduced after a short period of time, because no efforts were made to inhibit the enzymes that break down these molecules in the skin. Such commercial collagen peptides alone are not sufficient to reduce the rate of aging and age-related changes in the skin and other organs. In order to avoid the problems associated with the use of collagen peptides alone, this invention (called Collagen Daily) with enzyme inhibitors was invented.

MicroDaily EMF:

Most children are deficient in one or more micronutrients. 70% of US children and adolescents have suboptimal deficiency of vitamin D. 9% of them had vitamin D deficiency and 61% of them had insufficiency of vitamin D. Second-hand exposure to tobacco smoke induces vitamin D deficiency in 42% of US children. Vitamin D deficiency can cause rickets disease, interfere bone growth, increase the risk of heart disease, and cancer. Deficiency of vitamin A, vitamin C, vitamin D, vitamin E, and folate occurs in American children. 7% of 6 years and older have deficiency of vitamin C. 16 million are at risk of developing vitamin A deficiency.

In recent years, humans are being exposed to increased levels of man-made polarized electromagnetic field (EMF) radiation from devices, such as mobile phones, laptops, and Wi-Fi, microwave ovens, and television sets. Polarized EMF radiation induces vibration in charged molecules such as Na+, K+ Ca+ and others, whereas non-polarized EMF does not. The magnitude of vibrations of charged molecules depends upon the frequency of EMF radiation. Such vibration of charged molecules in the body can interfere with electrical communications between cells, especially in the brain and heart. This may be one of the mechanisms which accounts for acute health risks. Another mechanism involves increased production of free radicals and inflammation.

Children undergo physical growth and mental development such as cognitive function, emotional, and social skills. Micronutrient requirement is very high in children during this growth period. Even the deficit of one micronutrient can interfere with proper physical and mental development. Micronutrient deficiency may reduce immune function and increase the risk of chronic diseases. Micronutrient deficiency may reduce a child's ability to protect itself from EMF Radiation or other environmental exposures.

Most children are taking excessive amounts of junk foods, sugar rich beverages, and fats. Most children do not participate in physical activity. The above changes in diet and lifestyle leads to obesity as well as inadequate micronutrient intake contribute to micronutrient deficiency in children.

Commercially available multivitamins for children are totally inadequate. For example, none of them have endogenous (body-made antioxidants), such as coenzyme Q10, glutathione-elevating agents (alpha-lipoic acid and N-acetylcysteine), curcumin, resveratrol, quercetin, and selenium. These micronutrients are very important for proper growth and protection against environmental toxins. Other micronutrients, such as vitamin A, vitamin C, vitamin E, vitamin D, and all B-vitamins present at suboptimal levels. Therefore, these commercial multivitamin formulations are not sufficient to meet the needs of children during their growth period. Therefore, the present invention relates to a Micordaily-EMF for Kids in the form of gummy, which has all ingredients that are missing from the commercial multivitamin gummies for children. In addition, it has two forms of vitamin E (vitamin E succinate and vitamin E acetate). Folate and vitamin B12 are in methylated form. Doses are safe and effective.

The present invention may allow proper physical growth and mental development, and improve immune function leading to reduced risk of infection.

Why do children need a daily vitamin? Both Children and adults are exposed to the same environmental toxins, including EMF Radiation. However, their needs are in part different. Adults need adequate micronutrients to maintain a healthy body and mind during aging. Children need adequate micronutrients to ensure proper physical and mental development as well as to maintain them in a healthy condition during growth to adulthood. Even deficiency in one micronutrient can interfere with physical and mental growth of children. Factors, which contribute to deficiency include: poor diet (lack of fruits and vegetables); excessive consumption of junk food, fried food, and sugar; lack of physical activity; and obesity.

Supplementation with a scientifically prepared mixture of micronutrients together with good diet and physical activity would ensure the proper physical and mental development of children.

Commercially sold gummy vitamins have no endogenous (body-made antioxidants), such as coenzyme Q10, glutathione-elevating agents (alpha-lipoic acid and N-acetylcysteine), curcumin, resveratrol, quercetin, and selenium. They are very important micronutrients for proper growth and protection against environmental toxins. Other micronutrients are at suboptimal levels.

Prebiotic and Probiotics:

Even though Dr. Hippocrates, a physician, and a philosopher stated, "All diseases begin in the gut" some 2500 years ago, scientists became interested in investigating intestinal microorganisms and their role in human health and disease much later. It was not until the year 1880, when Dr. Theodor Escherich, an Austrian pediatrician, observed a bacterium (*Escherich coli*) in the intestines of healthy children and children who were suffering from diarrhea. Since then, identification and importance of microorganisms in the gut and other parts of the body continued. During the last two decades, several harmful and beneficial microorganisms were identified and their role in aging and age-related diseases including diabetes type II were studied. The current studies suggest that the intestines of normal individuals are colonized by a wide range of microbiota which include probiotics bacteria, viruses, fungi, and other micro-organisms. Beneficial probiotics bacteria include most species of *Bifidobacterial* and *Lactobacillus*, whereas harmful bacteria include some species of *Colostridium, Enterococcus, Staphylococcus, Bacteroides, E. coli, Helicobacter pylori*. The intestinal dysbiosis is defined by an imbalance in bacterial composition in which loss of beneficial bacteria, and overgrowth of potentially pathogenic bacteria occurs. The growth of harmful bacteria generates pro-inflammatory cytokines which are toxic to the cells, and deprive the body of certain B-vitamins, vitamin K, neurotransmitters, and short-chain fatty acids which are essential for maintaining good health. Intestinal dysbiosis is associated with Type 1 and Type 2 Diabetes. Intestinal dysbiosis also plays an important role in rapid progression of insulin resistance in diabetes type II. In addition, intestinal dysbiosis can decrease production of short-chain fatty acids such as butyric acid, propionic acid, and acetic acid due to decline in the number of butyric acid-producing bacteria in patients with diabetes type II. Butyric acid has diverse biological functions which include improving intestinal barrier integrity, pancreatic beta-cell proliferation, and insulin sensitivity, and reducing glycemia and body weight. Intestinal dysbiosis can also decrease production of other metabolites such as branched fatty acids which causes insulin resistance that can lead to the development of diabetes type II. Intestinal dysbiosis also causes inflammation and enhance intestinal permeability. Intestinal dysbiosis has been observed in animal models and in patients with diabetes type II and its complications such as retinopathy (eye damage), nephropathy (kidney damage), neuropathy (damage to peripheral Nerve), cardiovascular diseases, coronary artery disease (8). Severity of the gut dysbiosis is related to the severity of diabetes type II.

Therefore, restoring the composition of probiotics in favor of beneficial bacteria by probiotics with prebiotics would be needed to reduce the risk of diabetes type II and decrease the rate of progression of diabetes type I and type II. Administration of probiotics with prebiotics may reverse intestinal dysbiosis by increasing the number of beneficial bacteria and reducing the number of toxic bacteria, and thereby, reduce the risk of development and progression of diabetes. It is essential to add prebiotics with probiotics because they provide substrate to bacteria for fermentation which is necessary to produce short-chain fatty acids such as butyric acid.

SUMMARY OF THE INVENTION

In one embodiment, the present invention relates to a core four formulation system comprising at least one collagen system, at least one microdaily EMF system, at least one omega-3 system and at least one prebiotic and probiotic system with acid and heat resistant bacteria.

In another embodiment, the collagen system consisting of at least one collagen peptide, and at least one enzyme inhibitor, and at least one humectant, said at least one peptide are selected from a group consisting of bovine collagen peptides type I and bovine collagen peptides type III, and combinations and mixtures thereof, said at least one enzyme inhibitor selected from a group consisting of enzyme inhibitor from Amla fruit extract, enzyme inhibitor from white tea decaffeinated extract and combinations and mixtures thereof, and said at least one humectant is chosen from a group comprising hyaluronic acid, glycerin, pyrrolidone carboxylic acid, and mixtures and combinations thereof.

In yet another embodiment, the at least one peptide in the collagen formulation is in an amount from about 1 g to about 100 g by weight of said formulation. In still another embodiment, the at least one enzyme inhibitor in the collagen formulation is in an amount from about 10 mg to about 1,000 mg by weight of said formulation. In still yet another embodiment, the at least one humectant in the collagen formulation is in an amount from about 10 mg to about 500 mg by weight of said formulation. In a further embodiment, the collagen formulation should be taken at least once a day or at least twice a day. In another further embodiment, the collagen formulation consisting of: Bovine collagen peptides in an amount from about 1 g to about 100 g by weight of said formulation; amla fruit extract is in an amount from about 10 mg to about 1,000 mg by weight of said formulation; white tea decaffeinated extract is in an amount from about 10 mg to about 1,000 mg be weight of said formulation; Hyaluronic acid is an amount from about 10 mg to about 500 mg by weight of said formulation; and mixtures and combinations thereof.

In yet a further embodiment, the present invention relates to a Microdaily EMF formulation consisting of Vitamin A, Vitamin C, Vitamin D3, Vitamin E, Vitamin B1, Vitamin B2, Vitamin B3, Vitamin B5, Vitamin B6, Vitamin B7, Vitamin B12, folate, calcium, magnesium, zinc, selenium, chromium, N-acetylcysteine, Coenzyme Q10, alpha-lipoic acid, natural beta carotene, curcumin, trans-resveratrol, quercetin, and green tea extract.

In still a further embodiment, the EMF formulation consists of said Vitamin A is from about 1000 IU to about 10,000 IU, said Vitamin C is from about 50 mg to about 500 mg, said Vitamin D3 is from about 200 IU to about 1200 IU, said Vitamin E is from about 50 IU to about 400 IU, said Vitamin B1 is from about 2 mg to about 20 mg, said Vitamin B2 if from about 2 to about 20 mg, said Vitamin B3 is about 10 mg to about 100 mg, said Vitamin B5 is from about 2 mg to about 30 mg, said Vitamin B6 is from about 2 mg to about 15 mg, said Vitamin B7 is from about 5 mcg to about 50 mcg, said Vitamin B12 is from about 2 meg to about 20 mcg, said folate is from about 20 mcg to about 800 meg, said calcium is from about 30 mcg to about 250 mg, said magnesium is from about 30 mg to about 250 mg, said zinc is from about 5 mg to about 30 mg, said selenium is from about 50 mcg to about 300 mcg, said chromium is from about 10 mcg to about 100 mcg, said N-acetylcysteine is from about 50 mg to about 500 mg, said Coenzyme Q10 is from about 50 to about 400 mg, said alpha-lipoic acid is from about 50 mg to about 500 mg, said natural beta carotene is from about 10 mcg to about 250 mcg, said curcumin is from about 20 mg to about 400 mg, said Trans-resveratrol is from about 10 mg to about 250 mg, said Quercetin is from about 10 mg to about 200 mg, and said green tea extract is from about 10 mg to about 250 mg; all by weight of said formulation.

The EMF formulation of the present invention may be administered as a gummy vitamin that has all the ingredients that are missing from commercially sold children's gummy vitamins. It has two forms of vitamin E (vitamin E succinate and vitamin E acetate). The doses are safe and effective. It contains Folate and vitamin B12 in methylated form.

Expected benefits of the EMF product include: allows proper physical growth and mental development, improve immune function leading to reduced risk of infection and provide protection from EMF radiation and other environmental exposures; reduced hospital visit for children; reduced absentee from the school for children; positive interactions for children with teachers and peers; and positive interactions for children with all members of the family. prebiotic and probiotic system consisting of:

In another embodiment, the present invention provides for a prebiotic formulation consisting of Guar Gum, Inulin, Oat Beta Glucan, Larch Arabingalactan, Rice Flour, Apple Pectin and Fiber; and a probiotic formulation consisting of *Bifidobacterium longum, Lactobacillus rhamnosus, Lactobacillus salivarius, Lactobacillus acidophilus, Lactobacillus casei, Lactobacillus plantarum, Lactobacillus paracasei, Bifidobacterium breve, Bifidobacterium lactis, Bifidobacterium bifidum, Bifidobacterium infantis, Lactobacillus reuteri, Bacillus coagulans*, and *Saccharomyces Boulardii.*

In a further embodiment, the Bifedo and *Lactobacillus* strains of bacteria are acid sensitive and from about 60 to about 70% of said Bifedo and *Lactobacillus* strains of bacteria, when consumed, are killed by the acid pH of the stomach and the bile acid of the intestines. In another further embodiment, *Saccharomyces boulardii* and said *Bacillus Coagulans* are both acid and heat resistant and when consumed, said *Saccharomyces boulardii* and said *Bacillus Coagulans* survive the acid pH of the stomach and the bile acid of the intestines.

In another embodiment, the present invention relates to a formulation consisting of at least one dispersant, at least one beneficial probiotic and at least one prebiotic substrate wherein upon consumption of said formulation by a user, said at least one beneficial probiotic ferments said at least one prebiotic substrate, said at least one dispersant is used for creating small particles, said at least one beneficial probiotic is selected from the group consisting of *Bacillus coagulans, Saccharomyces boulardii, Lactobacillus* strain, *Bifedobacterial* strains, *Lactobacillus plantarum, Lactobacillus rhamnosus, Lactobacillus salivarius, Lactobacillus reuteri, Lactobacillus gasseri, Lactobacillus acidophilus, Lactobacillus casei, Lactobacillus paracasei, Bifedobacterial bifidum, Bifedobacterial animalis, Bifedobacterial longum, Bifedobacterial breve, Bifedobacterium infantis*, and combinations and mixtures thereof, said at least one prebiotic substrate is selected from the group consisting of apple pectin, guar gum, inulin, oat beta glucan, larch arabingalactan, rice flour, nonstarch polysaccharides, galacto-oligo saccharides, and transgalacto-oligosacchrides, combination and mixtures thereof, said dispersant is selected from the group consisting of magnesium stearate, rice flour, organic dispersants, inorganic dispersants, and combinations and mixtures thereof, wherein said Bifedo and *Lactobacillus* strains of bacteria are acid sensitive and from about 60 to about 70% of said Bifedo and *Lactobacillus* strains of bacteria, when consumed, are killed by the acid pH of the stomach and the bile acid of the intestines, and said *Saccharomyces boulardii* and said *Bacillus Coagulans* are both acid and heat resistant and when consumed, said *Saccharomyces boulardii* and said *Bacillus Coagulans* survive the acid pH of the stomach and the bile acid of the intestines.

In a further embodiment, the number of said at least one beneficial probiotic in said formulation is from about 10 CFU to about 25 CFU per dose. In yet a further embodiment, the number of said at least one prebiotic substrate in said formulation is from about 4 CFU to about 12 CFU per dose.

In still a further embodiment, a therapeutically effective amount of said formulation is intended to be administered once a day or twice a day. In still yet a further embodiment, a therapeutically effective amount of said formulation is intended to be administered to a patient with intestinal dysbiosis.

In another embodiment, the *Lactobacillus* strain is selected from the group consisting of *Lactobacillus rhamnosus, Lactobacillus salivarius, Lactobacillus acidophilus, Lactobacillus casei, Lactobacillus plantarum, Lactobacillus paracasei, Lactobacillus reuteri, Lactobacillus* gasseri, and combinations and mixtures thereof.

In a further embodiment, the *Bifedobacterial* strains is selected from the group consisting of *Bifedobacterium longum, Bifedobacterium breve, Bifedobacterium bifidum, Bifedobacterium infantis, Bifedobacterial animalis*, and combinations and mixtures thereof.

In another further embodiment, the probiotic formulation consisting of *Bifidobacterium longum, Lactobacillus rhamnosus, Lactobacillus salivarius, Lactobacillus acidophilus, Lactobacillus casei, Lactobacillus plantarum, Lactobacillus paracasei, Bifidobacterium breve, Bifidobacterium lactis, Bifidobacterium bifidum, Bifidobacterium infantis, Lactobacillus reuteri, Bacillus coagulans*, and *Saccharomyces Boulardii.*

In yet another further embodiment, the Bifedo and *Lactobacillus* strains of bacteria are acid sensitive and from about 60 to about 70% of said Bifedo and *Lactobacillus* strains of bacteria, when consumed, are killed by the acid pH of the stomach and the bile acid of the intestines.

In still another further embodiment, the *Saccharomyces boulardii* and said *Bacillus Coagulans* are both acid and heat resistant and when consumed, said *Saccharomyces boulardii* and said *Bacillus Coagulans* survive the acid pH of the stomach and the bile acid of the intestines.

In still yet another further embodiment, the present invention provides an omega-3 formulation consisting of a gelatin capsule, at least one anti-oxidation agent, docosahexaenoic acid (DHA) and eicosapentaenoic acid (EPA) derived from wild caught Omega-3 fish oil and having a ratio of at least 2:1, alpha-linolenic acid (ALA) derived from organic flaxseed oil and gamma-linolenic acid (GLA) derived from borage oil and having a ratio of at least 3:1, wherein said anti-oxidation agent, said docosahexaenoic acid, said eicosapentaenoic acid, said alpha-linolenic acid and said gamma-linolenic acid are the only therapeutically active agents in said composition, said gelatin capsule consists of bovine gelatin, glycerin and purified water, and said at least one anti-oxidation agent is selected from a group consisting of vitamin E, vitamin C, vitamin A, glutathione, and combination and mixtures thereof, wherein a therapeutically effective amount of said docosahexaenoic acid to said eicosapentaenoic acid in said ratio, and a therapeutically effective amount of said alpha-linolenic acid to said gamma-linolenic acid in said ratio, function to increase beneficial effects on the brain, heart, chronic inflammation, and cognitive function.

In another embodiment, the present invention provides for an Omega-3 system comprising therapeutically active agents, said therapeutically active agents consists of: at least one anti-oxidation agent, docosahexaenoic acid (DHA) and eicosapentaenoic acid (EPA), said DHA to EPA having a ratio of at least 2:1, alpha-linolenic acid (ALA) and gamma-linolenic acid (GLA), said ALA to GLA having a ratio of at least 3:1, said at least one anti-oxidation agent is selected from a group consisting of vitamin E, vitamin C, vitamin A, glutathione, and combination and mixtures thereof, said docosahexaenoic acid and eicosapentaenoic acid are selected from the group consisting of wild caught Omega-3 fish oil, fish oil selected from the group consisting of anchovy oil, cod liver oil, pollock oil, salmon oil, tuna oil, fish roe oil, krill oil, calanus oil, squid oil, and green-shelled mussel oil, fatty fish selected from the group consisting of salmon, tuna, mackerel, and pollock, forage fish selected from the group consisting of sardines, anchovies, herring, capelin and hoki, and algae selected from the group consisting of seaweed, nori, spirulina, sea moss, and chlorella, and combinations and mixtures thereof, said alpha-linolenic acid is selected from the group consisting of organic flaxseed oil, nuts, walnuts and combinations and mixtures thereof, and said gamma-linolenic acid is selected from the group consisting of borage oil, canola oil, vegetable oil, and combinations and mixtures thereof, wherein a therapeutically effective amount of said docosahexaenoic acid to said eicosapentaenoic acid in said ratio, and a therapeutically effective amount of said alpha-linolenic acid to said gamma-linolenic acid in said ratio, function to increase beneficial effects on the brain, heart, chronic inflammation, and cognitive function.

In another embodiment, a therapeutically effective amount of the probiotic system is intended to be administered to improve the brain function and improve glucose metabolism in the brain. In a further embodiment, said docosahexaenoic acid and said eicosapentaenoic acid function to increase high-density lipoprotein (HDL) cholesterol, decrease low-density lipoprotein (LDL) cholesterol and triglycerides, lower blood pressure, and maintain healthy heart. In another further embodiment, a therapeutically effective amount of said docosahexaenoic acid functions to improve brain function. In another embodiment, a therapeutically effective amount of said eicosapentaenoic acid functions to improve hearing health and brain health. In a further embodiment, a therapeutically effective amount of said alpha-linolenic acid functions primarily to increase energy, reduce inflammation, and improve heart health. In another further embodiment, a low effective amount of said gamma-linolenic acid functions to reduce inflammation and nerve pain.

In another embodiment, the Omega-3 formulation further comprises a gelatin capsule comprising bovine gelatin, glycerin and purified water. In a further embodiment, the Omega-3 formulation is in a form selected from the group consisting of capsule, liquid and pills.

In another further embodiment, the Omega-3 formulation comprising therapeutically active agents consisting of Vitamin E; docosahexaenoic acid (DHA) and eicosapentaenoic acid (EPA) derived from wild caught Omega-3 fish oil and having a ratio of at least 2:1; and alpha-linolenic acid (ALA) derived from organic flaxseed oil and gamma-linolenic acid (GLA) derived from borage oil and having a ratio of at least 3:1, wherein a therapeutically effective amount of said docosahexaenoic acid to said eicosapentaenoic acid in said ratio, and a therapeutically effective amount of said alpha-linolenic acid to said gamma-linolenic acid in said ratio, function to increase beneficial effects on the brain, heart, chronic inflammation, and cognitive function.

DETAILED DESCRIPTION OF THE INVENTION

As required, detailed embodiments of the present invention are disclosed herein; however, it is to be understood that the disclosed embodiments are merely exemplary of the invention that may be embodied in various forms. The figures are not necessarily to scale, some features may be exaggerated to show details of particular components. Therefore, specific structural and functional details disclosed herein are not to be interpreted as limiting, but merely as a basis for the claims and as a representative basis for teaching one skilled in the art to variously employ the present invention.

Collagen Formulation

The supplementation with collagen peptides alone is not sufficient to reduce the rate of aging and age-related changes in the skin and other organs for a prolonged period of time. This invention claimed to solve the problems associated with the use of collagen peptides alone.

During aging, the activities of enzymes collagenase, elastase, and hyaluronidase increase causing breakdown of collagen, elastin, and hyaluronic acid, respectively. This invention uses collagen peptides with inhibitors of enzymes and hyaluronic acid which would prevent the degradation of the levels of collagen, elastin, and hyaluronic acid in the skin. Therefore, Collagen Daily with enzyme inhibitors would lead to increased elasticity of the skin, reduced skin wrinkles and sagging, recovered lost cartilage tissue, decreased activity-related joint pain, strengthened tendons and ligaments, increased body mass in elderly men and premenopausal women, enhanced bone mineral density in post-menopausal women, and improved mobility and muscle function for a prolonged period of time.

This invention of Collagen Daily with enzyme inhibitors contains collagen peptides, inhibitors of enzymes from Amla fruit extract and white tea decaffeinated extract and sapodilla fruit extracts, and hyaluronic acid. Supplementation with Collagen Daily would reduce the rate of aging and age-related changes in the skin and other organs.

Oral supplementation with this invention (Collagen Daily) would elevate the levels of collagen and elastin, and while supplementation with hyaluronic acid would increase the levels of hyaluronic acid. If enzyme inhibitors are not used, these molecules would be degraded by their respective enzymes. Consequently, the beneficial effects of collagen peptides on aging would be markedly reduced. Therefore, it is essential to add inhibitors of enzymes in order to maintain their elevated levels for a long period of time. Two sources of enzyme inhibitors from Amla fruit extracts and white tea decaffeinated extracts were used because combinations of different enzyme inhibitors from these sources are more effective in preventing the degradation of collagen and elastin than that produced by one source. In another embodiment, sapodilla fruit extract could be used in preventing the degradation of collagen and elastin than that produced by one source.

The activities of enzymes collagenase, elastase, and hyaluronidase, which degrade collagen, elastin, and hyaluronic acid, increase during aging of the skin and other organs. This invention of Collagen Daily with enzyme inhibitors would prevent rise in the activities of these enzymes, and thereby, may reduce the rate of aging and age-related changes in the skin and other organs. This invention of Collagen Daily with enzyme inhibitors may produce following health benefits: (a) increases the levels of collagen, hydration, and elasticity of the skin, (b) reduces skin sagging and wrinkles, (c) recovers lost cartilage tissue, (d) strengthen tendon and ligament, (e) decreases joint pain, (f) improves bone mineral density in post-menopausal women, (g) improves memory by removing beta-amyloids, which kill cholinergic neurons responsible for storing memory, from the brain, (h) improves memory and learning ability by increasing the levels of BDNF (brain-derived neurotrophic factor), (i) improves symptoms of sarcopenia (loss of muscle as we grow older), (j) reduces osteoarthritis pain, (k) reduces symptoms of Rheumatoid arthritis, and (l) helps in wound healing.

In order to properly manufacture or create this invention, an individual must have the following qualifications: (a) Individual must have extensive knowledge of biochemical changes that are involved in aging; (b) Individual must have done research on recent advances in collagen function; (c) Individual must know about enzyme collagenase which inhibits collagen, elastase which inhibits elastin, and hyaluronidase which reduces hyaluronic acid. Elevated levels of collagen, elastin, and hyaluronic acid would reduce the rate of aging of the skin and other organs; (d) Individual must have done research on the sources of enzyme inhibitors and their role in aging; and (e) Individual must have a full knowledge of commercial collagen peptides that are being marketed, and have the ability to critically analyze the benefits and limitations of such products.

This invention (Collagen Daily) with enzyme inhibitors is prepared in a powder form. Take orally using a scoop that contains 11.6 g of product once-a-day for the remainder of the lifespan. The mixture of collagen peptides can be taken with water or any liquid.

Microdaily EMF

As stated above, there is no effective protective strategy for prevention of injury produced by EMF radiation. This invention claimed to solve this problem. This invention uses a comprehensive mixture of micronutrients, which would reduce acute and long-term adverse health effects of EMF radiation by attenuation oxidative stress and inflammation that contribute to increased risk of cancer, non-cancer diseases, neurological abnormalities, and reproductive system damage.

This invention differs from the use of a single micronutrient, which cannot protect both the aqueous and lipid environment of cells against EMF radiation. A single micronutrient cannot activate Nrf2 as well as increase in dietary and endogenous antioxidants that are required for optimally reducing oxidative and inflammatory damage. This invention proposes a novel concept of PAMARA (protection as much as reasonably achievable) against EMF radiation by using a comprehensive mixture of micronutrients. No such concept of protection against EMF radiation is available for humans.

Relationship Between the Components:

A comprehensive mixture of micronutrients contains vitamin A, vitamin C, vitamin E, vitamin D3, beta-carotene, alpha-lipoic acid, curcumin, resveratrol, coenzyme Q10, green tea extract, quercetin, all B-vitamins, and mineral selenium and zinc.

How the Invention Works:

EMF radiation causes damage by producing excessive amounts of free radicals (increased oxidative stress) and pro-inflammatory cytokines (inflammation). The proposed mixture of micronutrients would decrease oxidative stress and inflammation, and thereby, provide strong protection against EMF radiation damage.

Ionizing radiation such as X-ray or gamma-ray also causes damage by increasing oxidative stress and inflammation similar to those produced by EMF radiation, but at much higher levels than EMF radiation. This invention is based on my previous studies in which a mixture of micronutrients was very effective in reducing damage produced by ionizing radiation such as X-ray and gamma-ray compared to single antioxidants in animal models. In my previous study, a mixture of micronutrients such as proposed here was found to be safe in humans when administered orally.

How to Make Invention:

Individuals must have done research on the prevention and mitigation of damage produced by ionizing radiation. This person must have experience in research in micronutrients as well as ionizing radiation. This individual must have a full understanding of EMF radiation with respect to frequency range in Hz (Hertz), dose of EMF radiation in V/m (voltage/meter), and specific absorption rate (SAR) in W/kg (watt/kilogram).

All proposed antioxidants, B-vitamins, and minerals are essential for an optimal protection against EMF radiation damage. Iron, copper, manganese, and heavy metals are excluded. Vitamin E should be in the form of d-alpha-tocopheryl succinate, vitamin A in the form of retinol palmitate, and vitamin C in the form of calcium ascorbate. All vitamin E and beta-carotene should be in natural form.

This person must be aware of the research, which shows that iron, copper and manganese interact with vitamin C to generate extensive amounts of free radicals. Humans have no significant mechanisms of eliminating these trace minerals. Increased body store of one of these trace minerals enhances the risk of chronic diseases. Also, increased accumulation of heavy metals in the body could be neurotoxic. The body has a method of elimination of minerals or heavy metals.

How to Use Invention:

The proposed mixture of micronutrients is manufactured in the form of 6 capsules. Take orally 3 capsules in the morning with a meal and 3 capsules in the evening with a meal. Twice a day is recommended in order to maintain steady levels of micronutrients in the body.

EMF radiation increases the risk of acute and chronic adverse health effects by producing excessive amounts of free radicals and inflammation because of limitations of using a single antioxidant in humans, a mixture of micronutrients for protection against EMF (electromagnetic field) radiation damage is disclosed. Supplementation with this micronutrient mixture may reduce the risk of cancer, non-cancerous diseases, neurological abnormalities, and reproductive system damage produced by exposure to EMF radiation.

The advent of wireless communication technologies has led to increased exposure to EMF radiation that has enhanced risk of adverse health effects in humans. The introduction of 5G or 5th Generation wireless technology, which transmits signals at much higher frequency range (3-300 GHz) than previous generations, has raised further concerns about its impact on human health. No human studies on the effect of 5G infrastructures involving numerous antennae located in your neighborhood have been performed. Most epidemiologic studies showed that EMF radiation emitted from previous generations increased the risk of cancer in humans. Since extensive animal studies, and mechanistic studies in which EMF radiation increases the levels of markers of oxidative stress and inflammation, the above human studies can be considered valid. However, a few epidemiologic investigations have reported no increase in cancer risk following exposure to EMF radiation. The inconsistent epidemiologic studies on cancer risk could be due to the fact that the level of frequency, dose (strength) (voltage per meter or V/m), intensity (millitesla or mT), and SAR (specific absorption rate, Watts/Kg or W/Kg of tissue) were not comparable. Supplementation with individual antioxidants has reduced oxidative stress and protected against EMF radiation-induced damage. Because of limitations in implementing physical protection, a biological strategy for tissue protection should be developed. The major objectives of this review are to briefly describe (a) biological responses of 5G frequency range, (b) EMF radiation-induced cancer risk, and neurological and non-neurological damage, (c) the role of increased oxidative stress and inflammation in such damage, and (d) identify gaps in the knowledge. The review proposes a novel concept of PAMARA (protection as much as reasonably achievable) using a mixture of micronutrients for tissue protection against EMF radiation-induced damage.

During the course of evolution, humans have been exposed to background ionizing, non-ionizing radiation such as ultraviolet radiation and naturally occurring non-polarized EMF radiation. In recent years, they are being exposed to increased levels of man-made polarized electromagnetic field (EMF) radiation from devices, such as mobile phones, laptops, and Wi-Fi, microwave ovens, and television sets. Non-polarized EMF radiation cannot induce oscillation or vibrations in charged molecules such as Na, K Ca and others, whereas polarized EMF radiation induces such vibration. The magnitude of vibrations of charged molecules depends upon the frequency of EMF radiation. Such vibration of charged molecules in the body can interfere with electrical communications between cells, especially in the brain and heart. Therefore, Polarized EMF radiation induced vibration of charged particles in the body may represent one of the mechanisms that can increase health risks in humans. EMF radiation has been classified into extremely low frequency EMF (ELF-EMF), which has a frequency range up to 300 Hz, and radio frequency EMF (RF-EMF) with a frequency range of 3 KHz to 300 GHz).

The introduction of 5G or 5th Generation, the latest wireless technology, which transmits signals at frequency range between 30-300 GHz, has alarmed many health professionals and public because of its impact on increased adverse health effects in humans. There are some major differences between 5th Generation and previous generations technology. 5G utilizes millimeter waves (also called millimeter bands or extremely high frequency) and higher frequencies than the previous generations technologies. 5G EMF radiation can increase the risk of cancer, genetic damage, learning and memory deficits, and other neurological disorders.

The health effects of 5G frequency on humans have not been investigated. Most epidemiologic studies suggest that EMF radiation may increase the risk of cancer in humans. Animal studies supported the above conclusion. A few epidemiologic studies have reported no increase in cancer risk. The potential reasons for the above inconsistent results in humans are discussed later in this review.

Exposure to EMF radiation induced neurological abnormalities in some individuals, such as electromagnetic hypersensitivity, cognitive dysfunction, and abnormal electroencephalogram (EEG). It also caused non-neurological damage such as rise in blood pressure, and endocrine changes, sperm and testicular damage, ocular damage, and calcium overload. The exact mechanisms of EMF-induced these damages remain to be investigated.

Cell culture studies revealed that exposure to EMF radiation decreased the viability of cells, and increased chromosomal damage and double-strand DNA breaks. The changes in gene expression especially related to cancer, neurological and non-neurological diseases following exposure to EMF radiation have not been studied either on neuronal or non-neuronal cell culture.

Exposure to EMF radiation increased the levels of markers of oxidative damage in animals and humans and inflammation in animals. No studies on the levels of markers of inflammation in the blood of humans are available. Such studies should be conducted with appropriate attention to dose (V/m), intensity (mT), and energy absorption (SAR, W/kg). Since EMF radiation increases oxidative stress and inflammation, supplementation with antioxidants could reduce these cellular deficits. Indeed, a few studies showed that individual micronutrients before exposure to EMF radiation reduced adverse health effects in animal and cell culture models. No significant studies on the effects of administration of single or multiple micronutrients administered before exposure to EMF have been performed in humans.

At present, there are no guidelines for tissue protection against EMF radiation-induced damage in humans. For protection against ionizing radiation (x-ray or gamma-ray), we have proposed a novel concept of tissue protection with a mixture of micronutrients, but no specific recommendations were made in this study.

The major objectives of this review are to briefly describe (a) biological responses of 5G frequency range, (b) EMF radiation-induced cancer risk, and neurological and non-neurological damage, (c) the role of increased oxidative stress and inflammation in such damage, and (d) identify gaps in the knowledge. The review proposes a novel concept of PAMARA (protection as much as reasonably achievable) using a mixture of micronutrients for tissue protection against EMF radiation.

Biological Responses to 5G Frequency Range:

This 5G technology uses millimeter-waves, also known as extremely high frequency (EHF) waves, which transmits signals at frequency between 30 GHz-300 GHz. These frequencies are called millimeter waves because they have wavelengths between 1 mm and 10 mm, whereas radio waves transmit signals at frequency between 3 KHz to 300 GHz, and have longer wavelengths in centimeters.

The effects of millimeter waves on human health compared to radio waves have not been adequately investigated. A review of several studies revealed that millimeter waves increase skin temperature, alter gene expression, promote cell proliferation and synthesis of proteins linked with oxidative stress, and inflammatory responses. These changes could damage eye and neuromuscular activity. Another review analyzed 94 publications in vivo and in vitro on the health impact following exposure to frequency range between 6-100 GHZ). Eighty percent of the in vivo studies showed biological responses following exposure to EMF radiation, while 58% of the in vitro studies showed such responses. In vivo criteria of biological responses included alteration in physiological, neurological and histology parameters, whereas in vitro biological responses included changes in gene expression and protein synthesis, and enhanced cytotoxic effects, genotoxic effects, and temperature-related reactions. Operating frequency ranges of currently used wireless communication devices are presented in Table 1 below.

TABLE 1

Operating frequencies range of currently used wireless devices

| Types of Devices: | Frequency Ranges: |
|---|---|
| RF-EMF radiation | 3 KHz-300 GHz |
| EL-EMF radiation | 0-300 Hz |
| 5 G | 3-300 GHz |
| 4 G | 2-8 GHz |
| 3 G | 1885-2200 MHz |
| 2 G | 800-1900 MHz |
| 1 G | 450 MHz |
| WI-FI | 2.4 GHz |
| Mobil phone models | 1800-2200 MHz |
| Laptops | 1000-3600 MHz |

G = Generation
RF-EMF = Radiofrequency-Electromagnetic field. Transfer of energy by radiowaves
ELF-EMF = Extremely low frequency-electromagnetic field Effects of EMF Radiation on Cancer Risk:
Human Studies:

In 2011, an expert working group of the International Agency for Research on Cancer (IARC) defined RF-EMF radiation emitted from mobile phones or other wireless devices as Group 2B ("possible") human carcinogen. Several epidemiologic studies suggest that exposure to EMF radiation enhances the risk of glioma, acoustic neuroma, and meningioma. Ipsilateral use of mobile phones showed higher risk of these brain tumors on the side used than on the contralateral side. An elevated risk of these cancers tends to enhance with increasing latency, time of use, and with first exposure at the age 20 years and younger. Young women aged 21-39 years who were exposed to EMF radiation emitted from the Cell Phone kept in their brassieres at the rate of 10 h/day for several years developed an excess incidence of multifocal invasive cancer in the area of the breast immediately adjacent to the cell phones.

A few studies have reported no effect of EMF radiation emitted from mobile phones. The use of mobile phones by children and adolescents did not increase the incidence of brain tumors. The adult users of cellular phones and cordless phones did not show enhanced risk of glioma or meningioma. Exposure to RF-EMF radiation did not increase the risk of brain cancer (glioma and meningioma).

Animal Studies:

The US National Toxicology Program (NTP) has conducted comprehensive studies on the effects of EMF radiation exposure with 900 MHz in rats and with 1900 MHz in mice during pregnancy and during the entire lifespan of offspring on the incidence of cancer. These investigations showed that increased incidence of tumors, especially glioma and malignant schwannoma occur primarily in the cardiac nerves, but also in the brain. In addition, evidence of DNA damage was present in these organs (7-9). The results of these studies were questioned by the ICNIRP (International Commission on Non-Ionizing Radiation Protection). However NTP studies were supported by the Ramazzini Institute's investigations, which show that exposure to EMF radiation with 1800 MHz at the highest dose of 50 V/m (volts/meter) increased the incidence of tumor of the brain and heart in rats.

Some potential reasons for inconsistent epidemiologic investigations on cancer risk in humans following exposure to EMF radiation are discussed here. The health effects of EMF radiation depend upon the level of frequency, dose (strength) (voltage per meter or V/m), intensity (millitesla or mT), and energy absorption SAR (specific absorption rate, Watts/Kg of tissue). Higher the frequency, strength, intensity, and energy absorption greater would be the damage. Among these factors, the amount of energy absorption (SAR) is most critical in determining the extent of damage. These variables can easily be controlled in animal or cell culture studies, but it is very difficult to control them in human epidemiologic investigations. This difficulty may account for the controversy regarding EMF radiation-induced increase in cancer risk. Since epidemiologic studies on EMF radiation-induced cancer risk are supported by the animal studies and by the cellular mechanisms that participate in carcinogenesis processes, EMF radiation-induced cancer in humans is a valid conclusion.

Effects of EMF Radiation on Neurological Abnormalities:
EMF Radiation-Induced Hypersensitivity:

A review has described an early history of EMF-hypersensitivity. As early as in 1970, a study from the former Soviet Union described the "microwave syndrome" among military personnel, who were working with radio and radar equipment. This syndrome included fatigue, dizziness, headache, and inability to focus, cognitive impairment, and sleep disturbances. Similar symptoms were reported among Swedes employees, who worked in front of cathode ray tube monitors. Additional symptoms included flushing, burning, and tingling of the skin especially on the face, and photosensitivity. Similar symptoms were also reported from Finland following exposure to EMF radiation. EMF radiation-induced electromagnetic hypersensitivity is now referred to as idiopathic environmental intolerance (IEI) or electrohypersensitivity (EHS). The prevalence of EMF radiation hypersensitivity was 5-30% for mild cases, 1.5% to 5% for moderate cases, and 1.5% for severe cases. The prevalence of electromagnetic hypersensitivity was 1.55% in Sweden and 13.3% that decreased to 4.6% over a 5 year period in Taiwan.

Patients with hypersensitivity showed neurological symptoms that include headache, tinnitus, hyperacusis, dizziness, balance disorder, fibromyalgia, vegetative nerve dysfunction, and reduced cognitive capability, immediate memory loss, attention deficits, and eventually tempo-spatial confusion. These symptoms were associated with chronic insomnia, fatigue, depressive tendency, anxiety, emotional problems, and irritability.

The International Commission of Non-Ionizing Radiation Protection Report showed that daily RF-EMF radiation from cell phones for more than 50 minutes might increase the risk of early dementia or other thermal damage. Power plant workers, who were exposed to ELF-EMF radiation exhibited poor sleep quality, increased stress, depression, and anxiety. Swiss adolescents exposed to RF-EMF radiation in their head area exhibited decreased memory scores (verbal memory).

Exposure to mobile phone-EMF radiation for only 5-min impaired working memory, which was greater in 60 years or older individuals as well as in those who had mild cognitive impairment compared to healthy participants.

EMF-radiation-induced increases in the alpha band of electroencephalogram (EEG) were related to a rise in cerebral temperature in humans. Short-term exposure to RF-EMF radiation reduced EEG alpha power, but had no impact on cognitive function. Additional human studies are needed to define EMF radiation-induced biochemical and genetic changes that lead to electromagnetic hypersensitivity, cognitive dysfunction, and depression.

Mice exposed to 835 MHz EMF radiation at absorption of energy rate SAR (specific absorption rate) of 4.0 W/Kg of tissue exhibited increased autophagy, hyperactivity, and demyelination in the cortical neurons. Exposure to 900 MHz for 1 h per day for the entire adolescent period showed loss of pyramidal neurons in the hippocampus, and an increase in the levels of malondialdehyde and a decrease in catalase levels in rats. This suggests that EMF radiation-induced damage to the hippocampus was related to increased oxidative stress.

Neurons are electrically charged and exchange information with other neurons electronically. This is one of the mechanisms by which neurons conduct their normal function. EMF radiation alters this mechanism of communication that could induce damage to nerve cell function. Another method of communication between neurons is mediated by biochemical compounds.

Effects of EMF Radiation on Non-Neoplastic and Non-Neurological Damage:

A review of several studies on the effects of EMF radiation from Wi-Fi reported that such exposure caused increased oxidative stress, sperm/testicular damage, neuropsychiatric effects including EEG changes, apoptosis, DNA damage, endocrine changes, and calcium overload. Exposure of reproductive system to EMF radiation emitted by GSM (global System for Mobile Communication), which has frequency range of 2G and 2.5G, increased production of free radicals by increasing the activity of reduced nicotinamide adenine dinucleotide (NADH) oxidase in the cell membrane. Female rats exposed to 1800 MHz caused eye damage by upregulating the expression of caspase-2 and P38MAPK (p38 mitogen-activated protein kinase) in ocular cells.

Workers using mobile phones for 60 minutes showed increased systolic blood pressure compared to those who spent less time talking on the cell phones. Occupational stress tends to enhance further the levels of systolic blood pressure. The study further revealed that men exposed to EMF radiation showed an excess of blood pressure abnormalities, whereas women revealed more impairment of the ECG (electrocardiogram) profile. Additional investigations with larger sample size to evaluate the effect of EMF radiation on blood pressure are needed.

Effects of EMF Radiation on Cellular Damage:

Human peripheral blood lymphocytes were programmed to enter mitosis and then exposed to EMF radiation of 3G frequencies during the G2 phase of the cell cycle. The results showed that irradiated lymphocytes exhibited increased chromatid-type aberrations (gaps and breaks) an excess of up to 275% compared to unirradiated controls. Mouse spermatocyte cells (GC-2 cell line) were exposed to ELF-EMF radiation (50 Hz) intermittently (5 min on and 10 min off) at an intensity of 1, 2, or 3 millitesla (mT) or RF-EMF radiation (1800 MHz) at the specific absorption rate (SAR) of 1, 2, or 4 W/kg (watts/kg of tissue) for 24 hours. The results showed that neither ELF-EMF nor RF-EMF radiation affected the viability of cells. However, ELF-EMF radiation at the highest intensity of 3 mT increased double-strand DNA breaks, but RF-EMF did not. Furthermore, RF-EMF exposure at SAR of 4 W/kg increased oxidative damage to DNA bases, but exposure to ELF-EMF did not. Thus, both ELF-EMF and RF-EMF exposures caused DNA damage, which was dependent upon intensity and energy absorption, respectively. Mouse macrophages exposed to ELF-EMF with frequency of 50 Hz at the intensity of 1.0 millitesla (ImT) did not increase micronuclei formation, however, it enhanced the phagocytic activity of these cells.

A review has reported that individuals exposed to EMF radiation exhibited enhanced chromosomal damage in their lymphocytes or exfoliated buccal cells. However, one study found that mobile phone-EMF radiation exposure did not affect the levels of micronuclei in exfoliated buccal cells in humans. EMF radiation emitted from the cell phone induced DNA damage in the hair follicles in the ear canal. The levels of DNA damage were increased with daily increase in exposure time.

A few studies showed that EMF radiation produced no adverse effects. The reasons for these studies showing no adverse health effects of EMF radiations are not known. These studies have utilized different frequencies, dose (v/m), intensity (mT), and specific absorption rate in W/Kg, which may account for the above inconsistent results.

EMF Radiation Increases Oxidative Stress:

Human Studies:

A review has proposed that EMF radiation enhances production of mitochondria-generated free radicals in the reproductive systems of both men and women. High-voltage electricity generates ELF-EMF. Workers, who were chronically exposed to ELF-EMF, had elevated urine levels of 8-hydroxy-2-deoxyguanosine (8-OHdG) and F2-isoprostane compared to control groups. Oxidative stress following exposure to either ELF-EMF or RF-EMF radiation together with impaired DNA repair processes, repair mechanism, and other cellular damages can elevate the risk of development of cancer.

Exposure to ELF-EMF radiation emitted from high-voltage power lines increased oxidative stress as evidenced by elevated levels of urinary 8-isoprostane and 8-hydroxy-deoxyguanosine in workers. However, an investigation of the effects of ELF-EMF radiation did not show increased oxidative stress in workers performing tour-inspection near transformers and distribution power lines.

Animal Studies:

Exposure of immature and mature rats with 900 MHz 2 h/day for 45 days increased oxidative damage as evidenced by decreased glutathione levels and antioxidant enzyme activity, and increased levels of lipid peroxidation and nitric oxide in lymphoid organs. Immature rats showed higher levels of oxidative stress than mature rats. Acute exposure with ELF-EMF radiation increased oxidative stress in the brain as suggested by reduced activities of antioxidant enzymes catalase and superoxide dismutase in adult male rats, while it did not influence the levels of stress hormone corticosterone. Exposure of rat lymphocytes with 930 MHz at a SAR (specific absorption rate) rate of 1.5 W/kg did not change basal intracellular levels of free radicals; however, it enhanced the production of free radicals generated by FeCl2 (ferrous chloride). Rats exposed to 900 MHz for 30 min/day for 10 days showed increased oxidative damage in the kidney as evidenced by increased levels of MDA and decreased activities of antioxidant enzymes superoxide dismutase, catalase, and glutathione peroxidase. Continuous exposure with EMF radiation of 900 MHz for 1 h throughout adolescent period increased oxidative damage in the sciatic nerve cells of male rats. Male rats exposed to 1966.1 MHz at a dose of 4 mV/cm2 and SAR of 0.36 W/kg showed increased levels of oxidative stress, inflammation markers (IL-1beta, IL-6, and TNF-alpha compared to control animals. In addition, increased weight of adrenal gland and enhanced levels of stress hormones (adrenocorticotropic hormone and corticosterone were observed compared to controls. Exposure to 900 MHz and 1800 MHz induced significant increase in lipid peroxidation and reduction in level of glutathione in the testis and epididymis. Although no difference was found in total sperm count, sperm motility was significantly reduced, causing impaired fertility in animals exposed to EMF radiation.

EMF Radiation Enhances Chronic Inflammation:

Animals Exposed to 1800 MHz:

Rats with lipopolysaccharide (LPS)-induced neuroinflammation were exposed to head only with 1800 MHz EMF radiation for 2 hrs at a specific absorption rate of 1.55 W/kg. Levels of neuroinflammation induced by LPS were further enhanced in the auditory cortex concomitant with increased growth of microglia processes and reduced firing rates. In addition, a larger proportion of auditory cortex locations had high acoustic thresholds. However, these changes were not observed in animals not treated with LPS. This suggests that 2-hour exposure to mobile cell phones operating on a frequency of 1800 MHz does not induce inflammation in normal rats but that a second stressor may be needed. Experiments performed under similar experimental conditions with an increased SAR (specific absorption rate) of 2.9 W/kg also aggravated LPS-induced inflammation in the cerebral cortex. Exposure to EMF radiation with 900 MHz 45 min/day at an average specific absorption rate of 1.5 W/kg or 15 min/day at an average specific absorption rate of 6 W/kg emitted by mobile phones increased the levels of glial fibrillary acidic protein (GFAP), a marker of gliosis in the brain of rats (38). EMF radiation enhanced secretion of pro-inflammatory cytokines (TNF-alpha, IL-1 beta, and IL-6), and production of nitric oxide (NO), and reduced phagocytic activity of microglia cells (39). Exposure of microglia cells in culture (N9 microglia cells) to EMF radiation activated Janus kinase 2 (JAK2) and Signal Transducer and Activator of Transcription Protein-3 (STAT3) and enhanced binding ability of STAT3 to DNA. In addition, exposure to EMF radiation markedly increased the expression of markers of inflammation (CD11b, TNF-alpha, and iNOS) and production of NO. Treatment with pyridone 6, an inhibitor of JAK2, suppressed EMF radiation induced inflammatory responses.

Animals Exposed to 900 MHz:

A 15 minute exposure to 900 MHz from mobile phone at a SAR (specific absorption rate) of 6 W/kg activated glia cells as evidenced by increased levels of glial fibrillary acidic protein (GFAP) in a time-dependent manner in adult rat; however, it failed to produce similar effects in older rats, suggesting that the effect of EMF radiation of frequency of 900 MHz is age-dependent. EMF radiation emitted from mobile phones impaired immune function in rats. But this effect was mitigated by supplementation with vitamin D. Exposure to EMF radiation with 900 MHz in rats with elevated lipopolysaccharides-induced neuroinflammation during gestation or during adolescence did not influence behavior or further increase in inflammation in the brain. No studies on the levels of markers of inflammation in the blood of humans are available. Such studies should be conducted with appropriate attention to dose in V/m and specific absorption rate in W/kg).

How to Protect Human Tissues Against EMF Radiation and Other Harmful Environmental Factors:

Physical Protection Suggestions:

It is difficult to develop guidelines, because EMF radiation at varying levels is present all around in the environment, houses, and workplaces. The U.S. Federal Trade Commission Consumer Information report suggests increasing distance between EMF radiation source and recipient, reducing exposure time to EMF radiation, and shielding. These principles would be effective in reducing the dose of EMF radiation, if there is a single source of EMF radiation. However, there are multiple sources of EMF radiation therefore, these principles are difficult to implement. The claims of effectiveness of shielding products made by the commercial companies are false. In addition, the Federal Trade Commission report suggests that shielding may interfere with the cell phone signal, causing it to draw even more power in order to communicate with the cell phone tower (also called base station), probably exposing individuals to more EMF radiation. Because of limitations of utilizing the principles of physical protection against EMF radiation, it is essential that a biological strategy for tissue protection should be developed.

Biological Protection with Micronutrients:

Since EMF radiation increases oxidative stress and chronic inflammation, which contribute to EMF radiation-induced damage, effects of micronutrients on reducing the tissue damage were investigated. Most such studies were conducted with a single micronutrient. These studies are described here.

Human Studies:

Resveratrol and Green Tea:

Workers, who are chronically exposed to ELF-EMF radiation from high voltage electricity, exhibited increased oxidative stress. Treatment with resveratrol reduced this damage. Supplementation with green tea polyphenol reduced ELF-EMF radiation-induced oxidative stress in individuals working near the high-voltage power plants.

Animal Studies:

Melatonin and Omega-3-Fatty Acids:

Melatonin treatment prevented EMF radiation (900 MHz) induced oxidative damage in the kidney of rats. Prenatal exposure to 900 MHz EMF radiation together with melatonin or omega-3-fatty acids prevented EMF radiation-induced neuronal damage in the hippocampus of rats.

Luteolin:

Rats exposed to 900 MHz radiation showed reduced numbers of lending cells, primary spermatocytes, and spermatids compared to control animals. Treatment of animals with luteolin, a naturally occurring flavonoid with antioxidant and anti-inflammatory activity, enhanced the number of these cells compared to EMF irradiated animals not receiving luteolin.

Garlic Powder:

Exposure to 900 MHz at the average specific absorption rate of 1.08 for 1 h/day for 3 weeks increased the levels of MDA and advanced oxidation protein production in the brain; however, treatment with garlic powder, which exhibits antioxidant and anti-inflammation activities, reduced oxidative damage in the brain of rats.

Folic Acid:

Exposure to RF-EMF radiation of 900 MHz 60 min/day for 21 days caused reduction in the number of total pyramidal and granular cells in the hippocampus and dentate gyres and Purkinje cell number in the cerebellum of rats. Treatment with folic acid decreased these changes in the hippocampus and cerebellum.

Cell Culture Studies:

Curcumin:

Curcumin treatment of microglia cells in culture prevented EMF-induced elevation of pro-inflammatory cytokines and reduced phagocytic activity.

Vitamin A:

Exposure of porcine blood platelets to 1 KHz frequency emitted from liquid-crystal-display monitors at the intensity of 220 V/m for 30 and 60 minutes increased the levels of malondialdehyde (MDA); however, treatment with vitamin A significantly attenuated such changes.

Selenium:

Human embryonic kidney cells (HEK293) exposed to 2.4 GHz EMF radiation for 1 h revealed increased levels of MDA and decreased activities of superoxide dismutase (SOD) and glutathione peroxidase. In addition, the levels of apoptosis and caspase-3 activity were higher and Bcl2 were lower in EMF irradiated cells compared to controls. Treatment of these cells before EMF radiation exposure with selenium reduced such EMF radiation-induced biochemical changes.

The above limited studies show that micronutrients including antioxidants can reduce oxidative stress and reduce damage mostly in animal studies. Additional studies with individual and multiple micronutrients on reducing EMF radiation-induced damage should be performed. In the meanwhile, it is unlikely that a single micronutrient would be able to provide any significant protection in humans.

Limitations of Using Single Antioxidant in Protecting Against EMF Radiation Damage:

Although individual micronutrients have produced some benefits in experimental systems, it is unlikely that such an approach would be useful in reducing EMF radiation-induced damage in humans. The potential reasons include (a) different antioxidants are distributed differently in the sub-cellular compartments of cells; therefore, a single antioxidant cannot protect all parts of the cell; (b) administered single antioxidant in a high internal oxidative environment of EMF radiation exposed individuals becomes oxidized and then acts as a pro-oxidant; (c) an elevation of the levels of antioxidant enzymes and dietary and endogenous antioxidants is essential for reducing oxidative stress and inflammation, a single micronutrient cannot achieve this; (d) the affinity of different antioxidants for free radicals differs, depending upon their solubility; (e) both the aqueous and lipid compartments of the cell need to be protected together; a single antioxidant cannot meet this goal; (f) vitamin E is more effective in quenching free radicals in a reduced oxygenated cellular environment, whereas vitamin C and alpha-tocopherol are more effective in a higher oxygenated environment of the cells; (g) vitamin C is important for recycling the oxidized form of alpha-tocopherol to the antioxidant form; (h) different antioxidants alters the expression of different microRNAs each of which guides its respective mRNA to produce only protective proteins. For example, some antioxidants can activate Nrf2 by upregulating miR-200a that inhibits its target protein Keap1, whereas others activate Nrf2 by downregulating miR-21 that binds with 3-UTR Nrf2 mRNA.

Evidence for Failure of a Single Antioxidant in Human Studies:

Supplementation with a single antioxidant in humans did not produce those benefits that were observed in animal models. For example, administration of beta-carotene alone increased the risk of lung cancer in male heavy smokers. Vitamin E treatment was ineffective in patients with Alzheimer's disease, but it reduced the rate of decline in cognitive function in the early phase of this disease. Vitamin E was ineffective in heart disease on primary and most secondary outcomes. Thus, it is unlikely that the use of a single antioxidant would significantly reduce EMF radiation-induced damage.

Evidence for the Usefulness of a Mixture of Micronutrient in Human Studies:

Supplementation with a mixture of micronutrients produced beneficial effects in two clinical studies. For example, administration of multiple micronutrients reduced the risk of cancer in men and prolonged the time period for initiating the antiviral therapy in HIV infected patients. Therefore, it is highly likely that the proposed mixture would be effective in reducing acute and late adverse health effects following exposure to EMF radiation.

Proposed Concept of PAMARA (Protection as Much as Reasonably Achievable) for EMF Radiation Protection:

A novel biological concept PAMARA for tissue protection against EMF radiation damage is proposed. This concept suggests that administration of a mixture of micronutrients to individuals who are likely to receive EMF radiation doses may reduce its adverse health effects. A mixture of micronutrients containing vitamin A, mixed carotenoids, vitamin C, alpha-tocopheryl acetate, alpha-tocopheryl succinate, vitamin D3, alpha-lipoic acid, n-acetyl-cysteine, coenzyme Q10, omega-3-fatty acids, curcumin, resveratrol, quercetin, green tea extract, all B-vitamins, selenomethionine, and zinc is proposed. This mixture would increase the levels of antioxidant enzymes by activating a nuclear transcriptional factor Nrf2 and the levels of dietary and endogenous antioxidant compounds. These cellular changes are essential for optimal tissue protection against EMF radiation-induced damage. In one embodiment, the formulation for the proposed mixture of micronutrients and the dose per day of each micronutrient is presented in Table 2.

TABLE 2

Microdaily EMF formula

| Ingredients: | Dose per day: |
|---|---|
| Vitamin A (as palmitate) | 3000 IU (900 mcg) |
| Vitamin C (as calcium ascorbate, 80% vitamin C, 9.4% Ca) | 1000 mg |
| Vitamin D3 (as cholecalciferol) | 800 IU (10 mcg) |
| Vitamin E (as D-alpha-tocopherol succinate) | 200 IU (132 mg) |
| Vitamin E (as D-alpha-tocopherol acetate) | 200 IU (132 Mg) |
| Vitamin B1 (as thiamine mononitrate) | 4 mg |
| Vitamin B2 (as riboflavin) | 5 mg |
| Vitamin B3 (as niacinamide) | 30 mg |
| Vitamin B5 (as d-calcium pantothenate) | 10 mg |
| Vitamin B6 (as pyridoxin HCl) | 5 mg |
| Vitamin B7 (Biotin) | 200 mcg |
| Vitamin B12 (as methylcobalamine) | 10 mcg |
| Folate (as L-5-methyltetrahydrofolate, calcium) | 0.4 mg |
| Calcium (as citrate) | 125 mg |
| Magnesium (as citrate) | 75 mg |
| Zinc (as biglycinate chelate) | 15 mg |
| Selenium (as selenomethionine) | 100 mcg |
| Chromium (as picolinate) | 50 mcg |
| N-acetylcysteine | 250 mg |
| Coenzyme Q10 | 30 mg |
| Alpha-lipoic acid | 60 mg |
| Natural Beta carotene | 50 mcg RAE |
| Curcumin | 200 mg |
| Trans-resveratrol | 50 mg |
| Quercetin | 25 mg |
| Green tea extract | 25 mg |

In one embodiment, the formulation for the proposed mixture of micronutrients and the dose range per day of each micronutrient is presented in Table 3.

TABLE 3

| Microdaily-EMF Formula: | |
|---|---|
| Ingredients: | Dose Range Per Day: |
| Vitamin A (as palmitate) | 1000-10,000 IU |
| Vitamin C (as calcium ascorbate, 80% vitamin C, 9.4% Ca) | 50-500 mg |
| Vitamin D3 (as cholecalciferol) | 200-1200 IU |
| Vitamin E (as D-alpha-tocopherol succinate) | 50-400 IU |
| Vitamin E (as D-alpha-tocopherol acetate) | 50-400 IU |
| Vitamin B1 (as thiamine mononitrate) | 2-20 mg |
| Vitamin B2 (as riboflavin) | 2-20 mg |
| Vitamin B3 (as niacinamide) | 10-100 mg |
| Vitamin B5 (as d-calcium pantothenate) | 2-30 mg |
| Vitamin B6 (as pyridoxin HCl) | 2-15 mg |
| Vitamin B7 (Biotin) | 5-50 mcg |
| Vitamin B12 (as methylcobalamine) | 2-20 mcg |
| Folate (as L-5-methyltetrahydrofolate, calcium) | 20-800 mcg |
| Calcium (as citrate) | 30-250 mg |
| Magnesium (as citrate) | 30-250 mg |
| Zinc (as biglycinate chelate) | 5-30 mg |
| Selenium (as selenomethionine) | 50-300 mcg |
| Chromium (as picolinate) | 10-100 mcg |
| N-acetylcysteine | 50-500 mg |
| Coenzyme Q10 | 50-400 mg |
| Alpha-lipoic acid | 50-500 mg |
| Natural Beta carotene | 10-250 mcg RAE |
| Curcumin | 20-400 mg |
| Trans-resveratrol | 10-250 mg |
| Quercetin | 10-200 mg |
| Green tea extract | 10-250 mg |

Humans are being exposed to increased levels of electromagnetic field (EMF) radiation from various wireless communication technologies. Adverse health effects have been reported from exposure to EMF radiation. Introduction of 5G or 5th Generation technology, which transmits signals at frequency range between 3-300 GHz, has raised concerns about increased hazard to human health. No significant human studies on 5G EMF radiation have been performed.

Epidemiologic studies suggest that exposure to EMF radiation increases the risk of certain brain cancer. Animal studies have supported the above conclusion. A few epidemiologic investigations have reported that EMF radiation does not increase the risk of cancer. Some potential reasons for this inconsistent results could be that the level of frequency, dose (strength) (voltage per meter or V/m), intensity (millitesla of mT), and energy absorption SAR (specific absorption rate, Watts/Kg of tissue) were not comparable.

EMF radiation induces hypersensitivity in humans, who exhibit neurological syndromes that include fatigue, dizziness, headache, lack of concentration, cognitive impairment, and sleep disturbances. Pre-treatment with individual antioxidants reduced DNA damage, markers of oxidative damage and inflammation, and increased viability of neurons in the brain. Exposure of mammalian cells in culture to EMF radiation reduced cell viability in the brain and testis, and increased chromosomal aberrations. There are no controversies on EMF-induced neurological abnormalities. EMF radiation increases the levels of markers of oxidative damage and inflammation, which contribute to EMF radiation-induced damage.

Because of limitations of physical protection, a novel biological concept of PAMARA (protection as much as reasonably achievable) is proposed. This concept suggests that supplementation with a mixture of micronutrients may reduce EMF radiation-induced acute and late adverse health effects in humans.

EMF Radiation Increases Oxidative Stress:

A review has proposed that EMF radiation enhances production of mitochondria-generated free radicals in the reproductive systems of both men and women. Workers, who were chronically exposed to ELF-EMF, had elevated levels of markers of oxidative stress such as urine levels of 8-hydroxy-2-deoxyguanosine (8-OHdG) and F2-isoprostane compared to control groups. Exposure of immature and mature rats with 900 MHz 2 h/day for 45 days increased oxidative damage as evidenced by decreased glutathione levels and antioxidant enzyme activity, and increased levels of lipid peroxidation and nitric oxide in lymphoid organs. Immature rats showed higher levels of oxidative stress than mature rats. Acute exposure to EMF radiation increased oxidative stress in the brain as suggested by reduced activities of antioxidant enzymes catalase and superoxide dismutase in adult male rats. Rats exposed to 900 MHz for 30 min/day for 10 days showed increased oxidative damage in the kidney as evidenced by increased levels of MDA and decreased activities of antioxidant enzymes superoxide dismutase, catalase, and glutathione peroxidase. Male rats exposed to EMF radiation showed increased levels of oxidative stress and inflammation markers (IL-1beta, IL-6, and TNF-alpha) compared to control animals.

EMF Radiation Enhances Chronic Inflammation:

Exposure to EMF radiation with 900 MHz 45 min/day emitted by mobile phones increased the levels of glial fibrillary acidic protein (GFAP), a marker of gliosis in the brain of rats. EMF radiation enhanced secretion of pro-inflammatory cytokines (TNF-alpha, IL-1 beta, and IL-6), and production of nitric oxide (NO), and reduced phagocytic activity of microglia cells. In addition, exposure to EMF radiation markedly increased the expression of markers of inflammation (CD11b, TNF-alpha, and iNOS) and production of NO.

EMF Radiation-Induced Hypersensitivity:

The prevalence of EMF radiation hypersensitivity was 5-30% for mild cases, 1.5% to 5% for moderate cases, and 1.5% for severe cases. Patients with hypersensitivity showed neurological symptoms that include headache, tinnitus, hyperacusis, dizziness, balance disorder, fibromyalgia, vegetative nerve dysfunction, and reduced cognitive capability, immediate memory loss, attention deficits, and eventually tempo-spatial confusion. These symptoms were associated with chronic insomnia, fatigue, depressive tendency, anxiety, emotional problems, and irritability.

The International Commission of Non-Ionizing Radiation Protection Report showed that daily exposure to EMF radiation from cell phones for more than 50 minutes might increase the risk of early dementia or other thermal damage. Power plant workers, who were exposed to low levels of EMF radiation exhibited poor sleep quality, increased stress, depression, and anxiety. Exposure to mobile phone-EMF radiation for only 5-min impaired working memory, which was greater in 60 years or older individuals as well as in those who had mild cognitive impairment compared to healthy participants. Operating frequency ranges of currently used wireless communication devices are presented in Table 4.

TABLE 4

| Operating frequencies range of currently used wireless devices | |
|---|---|
| Types of devices | Frequency range |
| RF-EMF radiation | 3 KHz-300 GHz |
| EL-EMF radiation | 0-300 Hz |

TABLE 4-continued

Operating frequencies range of currently used wireless devices

| Types of devices | Frequency range |
|---|---|
| 5 G | 3-300 GHz |
| 4 G | 2-8 GHz |
| 3 G | 1885-2200 MHz |
| 2 G | 800-1900 MHz |
| 1 G | 450 MHz |
| WI-FI | 2.4 GHz |
| Mobile phone models | 1800-2200 MHz |
| Laptops | 1000-3600 MHz |

G = Generation

RF-EMF = Radiofrequency-Electromagnetic field. Transfer of energy by radio waves ELF-EMF = Extremely low frequency-electromagnetic field EMF Radiation-Induced Cancer:

In 2011, an expert working group of the International Agency for Research on Cancer (IARC) defined RF-EMF radiation emitted from mobile phones or other wireless devices as Group 2B ("possible") human carcinogen. Several epidemiologic studies suggest that exposure to EMF radiation enhances the risk of glioma, acoustic neuroma, and meningioma. Ipsilateral use of mobile phones showed higher risk of these brain tumors on the side used than on the contralateral side. An elevated risk of these cancers tends to enhance with increasing latency, time of use, and with first exposure at the age 20 years and younger. Young women aged 21-39 years who were exposed to EMF radiation emitted from the Cell Phone kept in their brassieres at the rate of 10 h/day for several years developed an excess incidence of multifocal invasive cancer in the area of the breast immediately adjacent to the cell phone.

The US National Toxicology Program (NTP) has conducted comprehensive studies on the effects of EMF radiation exposure with 900 MHz in rats and with 1900 MHz in mice during pregnancy and during the entire lifespan of offspring on the incidence of cancer. These investigations showed that increased incidence of tumors, especially glioma and malignant schwannoma occur primarily in the cardiac nerves, but also in the brain. In addition, evidence of DNA damage was present in these organs.

Epidemiologic studies on EMF radiation-induced cancer risk are supported by the animal studies and by the cellular mechanisms that participate in carcinogenesis processes, therefore, EMF radiation-induced cancer in humans is a valid conclusion.

EMF Radiation Induced Non-Neoplastic and Non-Neurological Damage:

A review of several studies on the effects of EMF radiation from Wi-Fi reported that such exposure caused increased oxidative stress, sperm/testicular damage, neuropsychiatric effects including EEG changes, apoptosis, DNA damage, endocrine changes, and calcium overload. Exposure of the reproductive system to EMF radiation increased production of free radicals by increasing the activity of reduced nicotinamide adenine dinucleotide (NADH) oxidase in the cell membrane. Female rats exposed to 1800 MHz caused eye damage by upregulating the expression of caspase-2 and P38MAPK (p38 mitogen-activated protein kinase) in ocular cells.

Workers using mobile phones for 60 minutes showed increased systolic blood pressure compared to those who spent less time talking on the cell phones. Occupational stress tends to enhance further the levels of systolic blood pressure. The study further revealed that men exposed to EMF radiation showed an excess of blood pressure abnormalities, whereas women revealed more impairment of the ECG (electrocardiogram) profile.

EMF Radiation-Induced Cellular Damage:

Exposure to EMF radiation from 3G frequencies showed that irradiated lymphocytes exhibited increased chromatid-type aberrations (gaps and breaks) an excess of up to 275% compared to unirradiated controls. EMF radiation exposure caused DNA damage, which was dependent upon intensity and energy absorption, respectively.

A review has reported that individuals exposed to EMF radiation exhibited enhanced chromosomal damage in their lymphocytes or exfoliated buccal cells. EMF radiation emitted from the cell phone induced DNA damage in the hair follicles in the ear canal. The levels of DNA damage were increased with daily increase in exposure time.

Suggestion of a Physical Protection Against EMF Radiation:

The US Federal Trade Commission Consumer Information report suggests that increasing distance between EMF radiation source and recipient, reducing exposure time to EMF radiation, and shielding would reduce the dose of EMF radiation, and thereby decrease the damage. This strategy is effective only if there is a single source of EMF radiation. However, there are multiple sources of EMF radiation therefore, these principles are difficult to implement. The claims of effectiveness of shielding products made by the commercial companies are false. In addition, a Federal Trade Commission report suggests that shielding may interfere with the cell phone signal, causing it to draw even more power to communicate with the cell phone tower (also called base station), probably exposing individuals to more EMF radiation. Because of limitations of utilizing the principles of physical protection against EMF radiation, it is essential that a biological strategy for tissue protection should be developed.

At present, there are no biological strategies for tissue protection against EMF radiation-induced damage in humans. For protection against ionizing radiation (x-ray or gamma-ray), we have proposed a novel concept of tissue protection with a mixture of micronutrients. Since EMF radiation increases oxidative stress and inflammation, supplementation with antioxidants could reduce these cellular deficits. Indeed, a few studies showed that individual micronutrients before exposure to EMF radiation reduced adverse health effects in animal and cell culture models.

Antioxidants Protect Against EMF Radiation Damage:

Since EMF radiation increases oxidative stress and chronic inflammation, which contribute to EMF radiation-induced damage, effects of antioxidants on reducing the tissue damage were investigated. Most such studies were conducted with a single antioxidant. These studies are described here.

Resveratrol and Green Tea:

Workers, who are chronically exposed to ELF-EMF radiation from high voltage electricity, exhibited increased oxidative stress. Treatment with resveratrol reduced this damage. Supplementation with green tea polyphenol reduced ELF-EMF radiation-induced oxidative stress in individuals working near the high-voltage power plants.

Omega-3-Fatty Acids:

Supplemented with omega-3-fatty acids during prenatal exposure to 900 MHz EMF radiation prevented EMF radiation-induced neuronal damage in the hippocampus of rats.

Folic Acid:

Exposure to RF-EMF radiation of 900 MHz 60 min/day for 21 days caused reduction in the number of total pyramidal and granular cells in the hippocampus and dentate gyres and Purkinje cell number in the cerebellum of rats.

Treatment with folic acid decreased these changes in the hippocampus and cerebellum.

Curcumin:

Curcumin treatment of microglia cells in culture prevented EMF-induced elevation of pro-inflammatory cytokines and reduced phagocytic activity.

Vitamin A:

Exposure of porcine blood platelets to EMF radiation delivered at 1 KHz frequency increased the levels of malondialdehyde (MDA), a marker of oxidative damage. Treatment with vitamin A significantly attenuated this damage.

Selenium:

Human embryonic kidney cells (HEK293) exposed to 2.4 GHz EMF radiation for 1 h revealed increased levels of MDA and decreased activities of superoxide dismutase (SOD) and glutathione peroxidase. Treatment of these cells before EMF radiation exposure with selenium reduced such EMF radiation-induced biochemical changes.

Limitations of Using Single Antioxidant in Protecting Against EMF Radiation Damage:

The potential reasons include: (a) different antioxidants are distributed differently in the subcellular compartments of cells; therefore, a single antioxidant cannot protect all parts of the cell; (b) administered single antioxidant in a high internal oxidative environment of EMF radiation exposed individuals becomes oxidized and then acts as a pro-oxidant; (c) an elevation of the levels of antioxidant enzymes and dietary and endogenous antioxidants is essential for reducing oxidative stress and inflammation, a single micronutrient cannot achieve this; (d) the affinity of different antioxidants for free radicals differs, depending upon their solubility; (e) both the aqueous and lipid compartments of the cell need to be protected together; a single antioxidant cannot meet this goal; (f) vitamin E is more effective in quenching free radicals in a reduced oxygenated cellular environment, whereas vitamin C and alpha-tocopherol are more effective in a higher oxygenated environment of the cells; and (g) vitamin C is important for recycling the oxidized form of alpha-tocopherol to the antioxidant form.

Evidence for Failure of a Single Antioxidant in Human Studies:

Supplementation with a single antioxidant in humans did not produce those benefits that were observed in animal models. For example, administration of beta-carotene alone increased the risk of lung cancer in male heavy smokers. Vitamin E treatment was ineffective in patients with Alzheimer's disease, but it reduced the rate of decline in cognitive function in the early phase of this disease. Vitamin E was ineffective in heart disease on primary and most secondary outcomes. Thus, it is unlikely that the use of a single antioxidant would significantly reduce EMF radiation-induced damage.

Evidence for the Usefulness of a Mixture of Micronutrient in Human Studies:

Supplementation with a mixture of micronutrients produced beneficial effects in two clinical studies. For example, administration of multiple micronutrients reduced the risk of cancer in men and prolonged the time period for initiating the antiviral therapy in HIV infected patients. Therefore, it is highly likely that proposed Microdaily EMF would be effective in reducing acute and late adverse health effects following exposure to EMF radiation.

Proposed Microdaily EMF for Protection Against EMF Radiation:

Proposed Microdaily containing vitamin A, mixed carotenoids, vitamin C, d-alpha-tocopheryl acetate, d-alpha-tocopheryl succinate, vitamin D3, alpha-lipoic acid, n-acetyl-cysteine, coenzyme Q10, omega-3-fatty acids, curcumin, resveratrol, quercetin, green tea extract, all B-vitamins, selenomethionine, and zinc is proposed. Microdaily EMF would increase the levels of antioxidant enzymes by activating a nuclear transcriptional factor Nrf2 and the levels of dietary and endogenous antioxidant compounds. These cellular changes are essential for optimal tissue protection against EMF radiation-induced damage.

What the Formulation Does:

Microdaily EMF simultaneously reduces oxidative stress and chronic inflammation by enhancing the levels of antioxidant enzymes and antioxidant compounds that are consumed from the diet and are made in the body. Microdaily EMF prevents the acute symptoms of EMF radiation-induced hypersensitivity, and thereby allows people to do their daily job. Microdaily EMF decreases the risk of late adverse effects of EMF radiation. Microdaily EMF protects against ionizing radiation such as x-ray, gamma-ray, and proton radiation.

Omega-3 Formulation

Omega 3 is a polyunsaturated fatty acid consisting of DHA (docosahexaenoic acid) and EPA (eicosapentaenoic acid) and ALA (alpha-linolenic acid) and are essential for brain function. It has an impact on cognitive function at all stages of life. Approximately, 50-60% of the brain weight are lipids, of which 35% consists of omega3 fatty acids. DHA accounts for more than 40% of total fatty acids in the brain, while EPA represents only 1% of total fatty acids. Omega-3 fatty acids reduce oxidative stress and chronic inflammation in the brain (13-15). A review of several clinical studies suggests that supplementation with omega-3-fatty acids enhances learning, memory, cognitive function, and blood flow in the brain. In addition, people who eat food with reduced amounts of omega-3 fatty acids, the elderly people, and lonelier individuals may derive benefits from Omega-3 supplement (16). Low intake of omega-3 fatty acids increases the risk of ADHD, autism, bipolar disorder, depression, and suicidal tendency (17). DHA/EPA promotes translocation of GLUT-4 from cytoplasmic vesicles to plasma membrane by causing phosphorylation of insulin-linked serine/thereonine protein kinase (AKT) in both normal and insulin resistance individuals (18). Translocated GLUT-4 allows entry of glucose in the adipocytes which use glucose for generating energy.

Sources of DHA and EPA: The major sources DHA and EPA include fish and other sea food, and algae which makes these polyunsaturated fatty acids. Among fishes, mackerel, salmon, herring, sardines, and caviar have high levels of DHA and EPA. Vegetarian diet contains ALA, but no DHA or EPA.

Conversion of Alpha-linolenic acid (ALA) to EPA and DHA, and EPA to DHA: Converted amount of ALA to EPA and DHA varies from one individual to another; however, converted amount of ALA to EPA and DHA is higher in women than in men. Healthy men convert 8% of ALA to EPA and only 0-4% of ALA is converted to DHA, whereas healthy women convert 21% ALA to EPA and only 9% of ALA is converted to DHA (19, 20). A small amount of EPA is converted to DHA in the liver, but reverse conversion does not occur.

The fact that supplemented with Omega-3 reduced oxidative stress, total lipid contents, and upregulated the expression of ATP synthase 6 gene suggested that DHA and EPA may exhibit anti-diabetic and anti-hypertension potential (21).

Omega-3-fatty acids: Our body needs essential fatty acids and non-essential fatty acids. Our body can make non-essential fatty acids like stearic acid, palmitic acid and arachidic acid, but our body cannot make essential fatty acids. We depend on these essential diets.

There are two types of essential fatty acids omega-3-fatty acids, and omega-6-fatty acids, also called linoleic acid. Linoleic acid is covered to gamma-linolenic acid (GLA).

Omega-3-fatty acids: There are three types of Omega-3-fatty acid EPA (Eicosapentaenoic acid) and DHA (docosahexaenoic acid) found in fatty fishes, ALA (alpha-linolenic acid) found in plant-based food. ALA is considered a precursor of EPA and DHA, but its conversion to EPA and DHA is extremely slow; therefore, it is stored and used for energy and other biological functions.

Omega-6-fatty acids: We consume omega-6-fatty acids, also called gamma-linolenic acid (GLA) is found in the plant-based food. GLA then breaks down to arachidonic acid which at high doses promotes inflammation, but at low doses reduced inflammation and nerve pain.

Importance of Ratio of Omega-6:Omega-3: The ratio of Omega-6:Omega-3 is important for optimal health. During the evolution of humans, the ratio was 1:1. Now, consumption of the American diet has increased this ration to 16:1. Higher levels of omega-6-fatty acids increase the risk of chronic diseases such as heart disease, while higher levels of omega-3 attenuate the risk of chronic diseases. Typical American diet has 14-25% more omega-6 than omega-3.

DHA, EPA, ALA, and antioxidants attenuate ADHD symptoms and further improve brain function. The proposed combination was more effective in reducing chronic inflammation and improving lipid profiles in the blood.

Overall benefits include: Improve brain function; Maintain healthy heart; Reduce chronic inflammation; Improve attention deficits; Reduce hyperactivity; Reduce Oxidative stress and inflammation in type II diabetes; Helpful in rheumatoid arthritis; and Helps with bipolar disorders.

Prebiotic and Probiotic Formulation

The word Probiotic comes from the Greek meaning "for life". The gut has a complex ecosystem in which nutrients, microbiota (refers to bacteria, viruses, and fungi), and host intestinal cells interact to improve human health. The probiotics are defined as microorganisms, which when administered in sufficient amounts provide health benefits to the host. Probiotics are live microorganisms that provide health benefits when consumed, generally by improving or restoring the gut microbiota. These live microorganisms are a combination of live beneficial bacteria and/or yeasts that naturally live in your body. Although viewed negatively, there are actually two forms of bacteria: good and bad bacteria. Probiotics are good bacteria that fight or balance the bad bacteria. When you are sick, bad bacteria has entered your body and multiplies in number, thereby knocking the body out of balance. Good bacteria or probiotics fights off the bad bacteria and restores balance within the body, making the individual feel better. In order to be a probiotic, it must include the following characteristics: be isolated from a human; survive in the intestine after digestion; have proven benefits; and can be consumed safely. The probiotics provide a plurality of health benefits: 1) probiotics help balance the friendly bacteria in the digestive system; 2) probiotics can help prevent and treat diarrhea; 3) probiotics may help improve mental health conditions; 4) certain probiotic strains can help with heart health; 5) probiotics may reduce the severity of certain allergies and eczema; 6) probiotics may help reduce symptoms of certain digestive disorders; 7) probiotic may help boost the immune system; and 8) probiotics may help you lose weight and belly fat.

For purposes of this invention, prebiotic is any substrate that is selectively utilized by host microorganisms conferring a health benefit. Often, prebiotics are types of soluble fibers that humans cannot digest but instead serve as "food" for beneficial microbes that already live in the colon or elsewhere in the body. Fructo-oligosacchrides (FOS), galacto-oligosaccharides (GOS), and transgalacto-oligosacchrides (TOS) are common prebiotics. Fermentation of prebiotics by gut microbiota produces short-chain fatty acids, including lactic acid, butyric acid and propionic acid.

Bifedo or *Lactobacillus* strains of bacteria which are acid sensitive and most of them (60-70%), when consumed, are killed by the acid pH of the stomach and the bile acid of the intestines. So for the purposes of this invention, *Saccharomyces boulardii* and *Bacillus Coagulans* play significant roles because they survive 100%. *Saccharomyces boulardii* and *Bacillus Coagulans* are both acid and heat resistant.

Probiotics Boost with Prebiotics has Following Beneficial Bacteria

1. *Saccharomyces boulardii*: This probiotic is a form of yeast derived from the fruit lychee. The fermented foods such as sauerkraut and kimchi are rich in *Saccharomyces boulardii*. It is superior to *Lactobacillus* and *Bifidobacterium*, because it is resistant to acid and temperature. The survival of this probiotic after gastric acidity is 75%. This probiotic grows optimally at 37° C. The stomach pH is around 2. *Lactobacillus* and *Bifedobacterial* strains are very sensitive to this acidic pH. *S. boulardii* prevents infection from harmful microorganisms, improve gut barrier function, symptoms of inflammatory bowel diseases, Crohn's disease, ulcerative colitis, immune function, and increase production of short chain fatty acid such as butyric acid during fermentation of insoluble and soluble fibers. This probiotic does not enter the bloodstream and is removed from the gut in 5 days.
2. *Lactobacillus* and *Bifidobacterial: Lactobacillus* strains and bifidobacterial strains decreased the risk of colorectal cancer, improve the symptoms of inflammatory bowel disease, and alcoholic and non-alcoholic fatty liver diseases, reduce the risk of obesity, type II diabetes, oxidative stress-related chronic diseases, and immune-mediated diseases. Combination of two probiotics decreased acute stress and depression. *Lactobacillus* inhibited pro-inflammatory cytokines and attachment of harmful bacteria. *Bifidobacterial* strains improved the symptoms of irritable bowel disorders, increased production of short-chain fatty acids, such as butyric during fermentation of insoluble and soluble fibers, which participated in reducing the risk of chronic diseases, and improved memory function.
3. *Bacillus Coagulans*: This probiotic is found in the intestine. These probiotics are resistant to acid and temperature. *Bacillus coagulans* improves digestion, inhibits the growth of pathogenic bacteria, promotes the ability to form spores which can survive in harsh environment of the gut, helps in forming B-vitamins, improves immune system, attenuates inflammatory bowel disease (IBD) and irritable bowel syndrome (IBS), produces short-chain fatty acids such as butyric acid, and reduces the risk of metabolic diseases such as obesity and type II diabetes.

Fermentation Product of Probiotics and Prebiotics

Butyric acid: Butyric acid is one of the short chain fatty acids, which is produced during fermentation of fibers by probiotics. Sodium butyrate inhibits the growth of cancer cells and enhances the effects of x-irradiation and chemotherapeutic agents. Importance of sodium butyrate was reviewed in 1980. Since then its beneficial effects were demonstrated in inflammatory bowel disorders by reducing pro-inflammatory cytokines, attenuates the risk of certain neurodegenerative diseases, diabetes, and cardiovascular diseases.

In one of the embodiments of the present invention, Table 1, set forth below, represents the ingredients, units, potency and dose for the Prebiotic formulation.

TABLE 1

| Prebiotic Formulation: Item Description: | | | |
|---|---|---|---|
| Active | Units | Potency | Dose |
| Guar Gum | 100 mg | 1.00 | 100.00 |
| Inulin | 150 mg | 1.00 | 150.00 |
| Oat Beta Glucan | 100 mg | 1.00 | 100.00 |
| Larch Arabingalactan | 100 mg | 1.00 | 100.00 |
| Rice Flour (Heat Treated) | 75 mg | | |

In another embodiment, Table 2 represents the ingredients, units, potency and dose for the Prebiotic and Probiotic formulation.

TABLE 2

| Prebiotic and Probiotic Formulation Item Description: | | | |
|---|---|---|---|
| Active | Units | Potency | Dose |
| *Bifidobacterium longum* (100B CFU/gm) | 2.65 Billion | 0.10 | 26.50 |
| *Lactobacillus rhamnosus* (200B CFU/gm) | 2.6 Billion | 0.20 | 13.00 |
| *Lactobacillus salivarius* (300B CFU/gm) | 2.6 Billion | 0.30 | 8.67 |
| *Lactobacillus acidophilus* La-14 (200B CFU/gm) | 2.5 Billion | 0.20 | 12.50 |
| *Lactobacillus casei* Lc-11 (300B CFU/gm) | 2.5 Billion | 0.30 | 8.33 |
| *Lactobacillus plantarum* (400B CFU/gm) | 1.78 Billion | 0.40 | 4.45 |
| *Lactobacillus paracasei* (400B CFU/gm) | 1.78 Billion | 0.40 | 4.45 |
| *Bifidobacterium breve* (300B CFU/gm) | 1.3 Billion | 0.30 | 4.33 |
| *Bifidobacterium lactis* (300B CFU/gm) | 1.3 Billion | 0.30 | 4.33 |
| *Bifidobacterium bifidum* Bb-06 (100B CFU/gm) | 1.29 Billion | 0.10 | 12.90 |
| *Bifidobacterium infantis* (50B CFU/gm) | 0.89 Billion | 0.05 | 17.80 |
| *Lactobacillus reuteri* (100B CFU/gm) | 0.42 Billion | 0.10 | 4.20 |
| *Bacillus coagulans* (NLT 100 billion spores/g) | 0.42 Billion | 0.10 | 4.20 |
| *Saccharomyces Boulardii* (20 B CFU/gm) | 0.085 Billion | 0.02 | 4.25 |
| Apple Pectin and Fiber | 50 mg | 1.00 | 50.00 |
| Guar Gum | 100 mg | 1.00 | 100.00 |
| Inulin | 150 mg | 1.00 | 150.00 |
| Oat Beta Glucan | 100 mg | 1.00 | 100.00 |
| Larch Arabingalactan | 100 mg | | |

In addition, the claimed invention is not directed to a product of nature. The combination of ingredients (dispersant, probiotic and prebiotic substrate) in the presently claimed invention is neither a product of nature or naturally occurring. Ingredients were specifically selected for particular performances, formulated to be a commercial product and the final formulation is admixed and encapsulated by a factory. The formulation of the presently claimed invention has characteristics or properties that are different from the naturally-occurring counterpart (in this case, the individual ingredients). For example, the formulation of the present invention "wherein upon consumption of said formulation by a user, said at least one beneficial probiotic ferment said at least one prebiotic substrate." The effectiveness of this formulation is in reversing the effects of intestinal dysbiosis (increased population of harmful bacteria and decline in the number of beneficial bacteria) and in the treatment and reduction of intestinal inflammatory bowel syndrome. The Bifedo and *Lactobacillus* strains of bacteria are acid sensitive and from about 60 to about 70% of said Bifedo and *Lactobacillus* strains of bacteria, when consumed, are killed by the acid pH of the stomach and the bile acid of the intestines, while the *Saccharomyces boulardii* and *Bacillus Coagulans* are both acid and heat resistant and when consumed, the *Saccharomyces boulardii* and *Bacillus Coagulans* survive the acid pH of the stomach and the bile acid of the intestines.

Among those benefits and improvements that have been disclosed, other objects and advantages of this invention will become apparent from the following description taken in conjunction with the accompanying drawings. The drawings constitute a part of this specification and include exemplary embodiments of the present invention and illustrate various objects and features thereof.

Numerous modifications and variations of the present invention are possible in light of the above teachings. It is therefore to be understood that within the scope of the attendant claims attached hereto, this invention may be practiced otherwise than as specifically disclosed herein.

What is claimed is:

1. A core four system consisting of at least one collagen system, at least one anti-radiation system, at least one polyunsaturated fatty-acid system and at least one prebiotic and probiotic system, said at least one collagen system consists of at least one peptide, and at least one enzyme inhibitor, and at least one humectant, said at least one peptide are selected from a group consisting of bovine collagen peptides type I and bovine collagen peptides type III, and combinations and mixtures thereof, said at least one enzyme inhibitor selected from a group consisting of enzyme inhibitor from Amla fruit extract, enzyme inhibitor from white tea decaffeinated extract and combinations and mixtures thereof, and said at least one humectant is chosen from a group comprising hyaluronic acid, glycerin, pyrrolidone carboxylic acid, and mixtures and combinations thereof, said at least anti-radiation system consists of Vitamin A, Vitamin C, Vitamin D3, Vitamin E, Vitamin B1, Vitamin B2, Vitamin B3, Vitamin B5, Vitamin B6, Vitamin B7, Vitamin B12, folate, calcium, magnesium, zinc, selenium, chromium, N-acetylcysteine, Coenzyme Q10, alpha-lipoic acid, natural beta carotene, curcumin, trans-resveratrol, quercetin, and green tea extract, said unsaturated fatty acid system consists of a gelatin capsule, at least one anti-oxidation agent, docosahexaenoic acid (DHA) and eicosapentaenoic acid (EPA) derived from wild caught Omega-3 fish oil and having a ratio of at least 2:1, alpha-linolenic acid (ALA) derived from organic flaxseed oil and gamma-linolenic acid (GLA) derived from borage oil and having a ratio of at least 3:1, wherein said anti-oxidation agent, said docosahexaenoic acid, said eicosapentaenoic acid, said alpha-linolenic acid and said gamma-linolenic acid are the only therapeutically active agents in said composition, said gelatin capsule consists of bovine gelatin, glycerin and purified water, and said at least one anti-oxidation agent is selected from a group consisting of vitamin E, vitamin C, vitamin A, glutathione, and combination and mixtures thereof, and said prebiotic and probiotic system consists of at least one dispersant, at least one beneficial probiotic and at least one prebiotic substrate wherein upon consumption of said formulation by a user, said at least one beneficial probiotic ferments said at least one prebiotic substrate, said at least one dispersant is used for creating small particles, said at least one beneficial probiotic is selected from the group consisting of *Bacillus coagulans, Saccharomyces boulardii, Lactobacillus* strain, *Bifedobacterial* strains, *Lactobacillus plantarum, Lactobacillus rhamnosus, Lactobacillus salivarius, Lactobacillus reuteri, Lactobacillus gasseri, Lactobacillus acidophilus, Lactobacillus casei, Lactobacillus paracasei, Bifedobacterial bifidum, Bifedobacterial animalis, Bifedobacterial longum, Bifedobacterial breve, Bifedobacterium infantis*, and combinations and mixtures thereof said at least one prebiotic substrate is selected from the group consisting of apple pectin, guar gum, inulin, oat beta glucan, larch arabingalactan, rice flour, nonstarch polysaccharides, galacto-oligo saccharides, and transgalacto-oligosacchrides, combination and mixtures thereof, said dispersant is selected from the group consisting of magnesium stearate, rice flour, organic dispersants, inorganic dispersants, and combinations and mixtures thereof, wherein said Bifedo and *Lactobacillus* strains of bacteria are acid sensitive and from about 60 to about 70% of said Bifedo and *Lactobacillus* strains of bacteria, when consumed, are killed by the acid pH of the stomach and the bile acid of the intestines, and said *Saccharomyces boulardii* and said *Bacillus Coagulans* are both acid and heat resistant and when consumed, said *Saccharomyces boulardii* and said *Bacillus Coagulans* survive the acid pH of the stomach and the bile acid of the intestines.

2. The system of claim 1 wherein at least one peptide in the collagen formulation is in an amount from about 1 g to about 100 g by weight of said polyunsaturated fatty-acid system, said at least one enzyme inhibitor in the collagen formulation is in an amount from about 10 mg to about 1,000 mg by weight of said omega-3 system, and said at least one humectant in the collagen formulation is in an amount from about 10 mg to about 500 mg by weight of said omega-3 system.

3. The system of claim 1 wherein said at least one anti-radiation system consists of said Vitamin A is from about 1000 IU to about 10,000 IU by weight of said anti-radiation system, said Vitamin C is from about 50 mg to about 500 mg by weight of said anti-radiation system, said Vitamin D3 is from about 200 IU to about 1200 IU by weight of said anti-radiation system, said Vitamin E is from about 50 IU to about 400 IU by weight of said anti-radiation system, said Vitamin B1 is from about 2 mg to about 20 mg by weight of said anti-radiation system, said Vitamin B2 if from about 2 to about 20 mg by weight of said anti-radiation system, said Vitamin B3 is about 10 mg to about 100 mg by weight of said EMP anti-radiation system, said Vitamin B5 is from about 2 mg to about 30 mg by weight of said anti-radiation system, said Vitamin B6 is from about 2 mg to about 15 mg by weight of said anti-radiation system, said Vitamin B7 is from about 5 mcg to about 50 mcg by weight of said anti-radiation system, said Vitamin B12 is from about 2 mcg to about 20 mcg by weight of said anti-radiation system, said folate is from about 20 mcg to about 800 mcg by weight of said anti-radiation system, said calcium is from about 30 mcg to about 250 mg by weight of said anti-radiation system, said magnesium is from about 30 mg to about 250 mg by weight of said anti-radiation system, said zinc is from about 5 mg to about 30 mg by weight of said anti-radiation system, said selenium is from about 50 mcg to about 300 mcg by weight of said anti-radiation system, said chromium is from about 10 mcg to about 100 mcg, said N-acetylcysteine is from about 50 mg to about 500 mg by weight of said anti-radiation system, said Coenzyme Q10 is from about 50 to about 400 mg by weight of said anti-radiation system, said alpha-lipoic acid is from about 50 mg to about 500 mg by weight of said EMP anti-radiation system, said natural beta carotene is from about 10 mcg to about 250 mcg by weight of said anti-radiation system, said curcumin is from about 20 mg to about 400 mg by weight of said anti-radiation system, said Trans-resveratrol is from about 10 mg to about 250 mg by weight of said anti-radiation system, said Quercetin is from about 10 mg to about 200 mg by weight of said anti-radiation system, and said green tea extract is from about 10 mg to about 250 mg by weight of said anti-radiation system.

4. The system of claim 1 wherein the number of said at least one beneficial probiotic in said formulation is from about 10 CFU to about 25 CFU per dose, and the number of said at least one prebiotic substrate in said formulation is from about 4 CFU to about 12 CFU per dose.

5. The system of claim 1 wherein said *Lactobacillus* strain is selected from the group consisting of *Lactobacillus rhamnosus, Lactobacillus salivarius, Lactobacillus acidophilus, Lactobacillus casei, Lactobacillus plantarum, Lactobacillus paracasei, Lactobacillus reuteri, Lactobacillus gasseri*, and combinations and mixtures thereof.

6. The system of claim 1 wherein *Bifedobacterial* strains is selected from the group consisting of *Bifedobacterium longum, Bifedobacterium breve, Bifedobacterium bifidum, Bifedobacterium infantis, Bifedobacterial animalis*, and combinations and mixtures thereof.

7. A core four dietary supplement system consisting of:

at least one collagen system consisting of at least one peptide, and at least one enzyme inhibitor, and at least one humectant, said at least one peptide are selected from the group consisting of bovine collagen peptides type I and bovine collagen peptides type III, and combinations and mixtures thereof, said at least one enzyme inhibitor selected from the group consisting of enzyme inhibitor from Amla fruit extract, enzyme inhibitor from white tea decaffeinated extract and combinations and mixtures thereof, and said at least one humectant is selected from the group consisting of hyaluronic acid, glycerin, pyrrolidone carboxylic acid, and mixtures and combinations thereof;

at least one anti-radiation system consisting of Vitamin A, Vitamin C, Vitamin D3, Vitamin E, Vitamin B1, Vitamin B2, Vitamin B3, Vitamin B5, Vitamin B6, Vitamin B7, Vitamin B12, folate, calcium, magnesium, zinc, selenium, chromium, N-acetylcysteine, Coenzyme Q10, alpha-lipoic acid, natural beta carotene, curcumin, trans-resveratrol, quercetin, and green tea extract;

a digestive support system consisting of a prebiotic and probiotic portion, said prebiotic portion consisting of Guar Gum, Inulin, Oat Beta Glucan, Larch Arabingalactan, Rice Flour, Apple Pectin and Fiber; and a probiotic formulation consisting of *Bifidobacterium longum, Lactobacillus rhamnosus, Lactobacillus salivarius, Lactobacillus acidophilus, Lactobacillus casei, Lactobacillus plantarum, Lactobacillus paracasei, Bifidobacterium breve, Bifidobacterium lactis, Bifidobacterium bifidum, Bifidobacterium infantis, Lactobacillus reuteri, Bacillus coagulans*, and *Saccharomyces Boulardii*, and said probiotic portion consisting of *Bifidobacterium longum, Lactobacillus rhamnosus, Lactobacillus salivarius, Lactobacillus acidophilus, Lactobacillus casei, Lactobacillus plantarum, Lactobacillus paracasei, Bifidobacterium breve, Bifidobacterium lactis, Bifidobacterium bifidum, Bifidobacterium infantis, Lactobacillus reuteri, Bacillus coagulans*, and *Saccharomyces Boulardii*; and a polyunsaturated fatty-acid system comprising therapeutically active agents, said therapeutically active agents consists of: at least one anti-oxidation agent, docosahexaenoic acid (DHA) and eicosapentaenoic acid (EPA), said DHA to EPA having a ratio of at least 2:1, alpha-linolenic acid (ALA) and gamma-linolenic acid (GLA), said ALA to GLA having a ratio of at least 3:1, said at least one anti-oxidation agent is selected from a group consisting of vitamin E, vitamin C, vitamin A, glutathione, and combination and mixtures thereof, said docosahexaenoic acid and eicosapentaenoic acid are selected from the group consisting of wild caught Omega-3 fish oil, fish oil selected from the group consisting of anchovy oil, cod liver oil, pollock oil, salmon oil, tuna oil, fish roe oil, krill oil, calanus oil, squid oil, and green-shelled mussel oil, fatty fish selected from the group consisting of salmon, tuna, mackerel, and pollock, forage fish selected from the group consisting of sardines, anchovies, herring, capelin and hoki, and algae selected from the group consisting of seaweed, nori, *spirulina*, sea moss, and *chlorella*, and combinations and mixtures thereof, said alpha-linolenic acid is selected from the group consisting of organic flaxseed oil, nuts, walnuts and combinations and mixtures thereof, and said gamma-linolenic acid is selected from the group consisting of borage oil, canola oil, vegetable oil, and combinations and mixtures thereof.

8. The system of claim 7 wherein the Bifedo and *Lactobacillus* strains of bacteria in said digestive support system are acid sensitive and from about 60 to about 70% of said Bifedo and *Lactobacillus* strains of bacteria, when consumed, are killed by the acid pH of the stomach and the bile acid of the intestines.

9. The system of claim 7 wherein the *Saccharomyces boulardii* and said *Bacillus Coagulans* in said digestive support system are both acid and heat resistant and when consumed, said *Saccharomyces boulardii* and said *Bacillus Coagulans* survive the acid pH of the stomach and the bile acid of the intestines.

10. The system of claim 7 wherein said collagen system consists of: Bovine collagen peptides in an amount from about 1 g to about 100 g by weight of said collagen system; Amla fruit extract is in an amount from about 10 mg to about 1,000 mg by weight of said collagen system; White tea decaffeinated extract is in an amount from about 10 mg to about 1,000 mg by weight of said collagen system; Hyaluronic acid is an amount from about 10 mg to about 500 mg by weight of said collagen system; and mixtures and combinations thereof.

11. The system of claim 7 wherein the Bifedo and *Lactobacillus* strains of bacteria in said digestive support system are acid sensitive and from about 60 to about 70% of said Bifedo and *Lactobacillus* strains of bacteria, when consumed, are killed by the acid pH of the stomach and the bile acid of the intestines.

12. The system of claim 7 wherein said polyunsaturated fatty-acid system further comprises a gelatin capsule comprising bovine gelatin, glycerin and purified water.

13. The system of claim 7 wherein each of said systems is in a form selected from the group consisting of capsule, liquid, gels, gummies and pills.

14. A core four system consisting of:

at least one collagen system consisting of therapeutically active agents consisting of at least one peptide, and at least one enzyme inhibitor, and at least one humectant, said at least one peptide are selected from the group consisting of bovine collagen peptides type I and bovine collagen peptides type III, and combinations and mixtures thereof, said at least one enzyme inhibitor selected from the group consisting of enzyme inhibitor from Amla fruit extract, enzyme inhibitor from white tea decaffeinated extract and combinations and mixtures thereof, and said at least one humectant is selected from the group consisting of hyaluronic acid, glycerin, pyrrolidone carboxylic acid, and mixtures and combinations thereof;

at least one anti-radiation system consisting of therapeutically active agents consisting of Vitamin A, Vitamin C, Vitamin D3, Vitamin E, Vitamin B1, Vitamin B2, Vitamin B3, Vitamin B5, Vitamin B6, Vitamin B7, Vitamin B12, folate, calcium, magnesium, zinc, selenium, chromium, N-acetylcysteine, Coenzyme Q10, alpha-lipoic acid, natural beta carotene, curcumin, trans-resveratrol, quercetin, and green tea extract;

a digestive support system consisting of a prebiotic and probiotic therapeutically active agents, said therapeutically active agents for said prebiotic portion consisting of Guar Gum, Inulin, Oat Beta Glucan, Larch Arabingalactan, Rice Flour, Apple Pectin and Fiber; and a probiotic formulation consisting of *Bifidobacterium longum, Lactobacillus rhamnosus, Lactobacillus salivarius, Lactobacillus acidophilus, Lactobacillus casei, Lactobacillus plantarum, Lactobacillus paracasei, Bifidobacterium breve, Bifidobacterium lactis, Bifidobacterium bifidum, Bifidobacterium infantis, Lactobacillus reuteri, Bacillus coagulans*, and *Saccharomyces Boulardii*, and said therapeutically active agents for said probiotic portion consisting of *Bifidobacterium longum, Lactobacillus rhamnosus, Lactobacillus salivarius, Lactobacillus acidophilus, Lactobacillus casei, Lactobacillus plantarum, Lactobacillus paracasei, Bifidobacterium breve, Bifidobac-*

*terium lactis, Bifidobacterium bifidum, Bifidobacterium infantis, Lactobacillus reuteri, Bacillus coagulans*, and *Saccharomyces Boulardii*; and a polyunsaturated fatty-acid system consisting of therapeutically active agents consisting of Vitamin E; docosahexaenoic acid (DHA) and eicosapentaenoic acid (EPA) derived from wild caught Omega-3 fish oil and having a ratio of at least 2:1; and alpha-linolenic acid (ALA) derived from organic flaxseed oil and gamma-linolenic acid (GLA) derived from borage oil and having a ratio of at least 3:1.

* * * * *